United States Patent [19]
Kieval et al.

[11] Patent Number: 5,626,623
[45] Date of Patent: May 6, 1997

[54] METHOD AND APPARATUS FOR OPTIMIZING PACEMAKER AV DELAY

[75] Inventors: Robert S. Kieval, Golden Valley; Tommy D. Bennett, Shoreview, both of Minn.

[73] Assignee: Medtronic, Inc., Minneapolis, Minn.

[21] Appl. No.: 640,434

[22] Filed: Apr. 30, 1996

[51] Int. Cl.$^6$ ................................................. A61N 1/36
[52] U.S. Cl. ........................................................ 607/23
[58] Field of Search ................................ 607/9, 14, 23, 607/24, 25

[56] References Cited

U.S. PATENT DOCUMENTS

| | | |
|---|---|---|
| 4,108,148 | 8/1978 | Cannon . |
| 4,303,075 | 12/1981 | Heilman . |
| 4,566,456 | 1/1986 | Koning . |
| 4,730,619 | 3/1988 | Koning . |
| 4,899,751 | 2/1990 | Cohen . |
| 4,899,752 | 2/1990 | Cohen . |
| 4,936,304 | 6/1990 | Kresh . |
| 5,003,976 | 4/1991 | Alt . |
| 5,154,170 | 10/1992 | Bennett . |
| 5,158,078 | 10/1992 | Bennett . |
| 5,163,429 | 11/1992 | Cohen . |
| 5,282,839 | 2/1994 | Roline . |
| 5,330,511 | 7/1994 | Boute . |

OTHER PUBLICATIONS

"Monitoring of Pulmonary Arterial Diastolic Pressure Through a Right Ventricular Pressure Transducer", Ohlsson et al., J. of Cardiac Failure, vol. 1, No. 2, 1995, p. 161.

"Initial Experience with an Implantable Hemodynamic Monitor", Steinhaus et al., Circulation vol. 93, No. 4, Feb. 15, 1996, p. 745.

"Measurement of Pulmonary Artery Diastolic Pressure from the Right Ventricle", Reynolds, et al., JACC, vol. 25. No. 5, Apr. 1955 p. 1176.

*Primary Examiner*—William E. Kamm
*Assistant Examiner*—Scott M. Getzow
*Attorney, Agent, or Firm*—Michael B. Atlass; Harold R. Patton

[57] ABSTRACT

In a dual chamber cardiac pacemaker, a method and apparatus for determining an atrioventricular (AV) delay interval to maintain optimal left heart AV mechanical synchrony and function. When the intrinsic or paced atrial heart rate is stable, test AV delay intervals are selected and delivered as right ventricular absolute blood pressures (RVP) are measured at the opening of the pulmonary valve. The opening of the pulmonary valve is determined by the peak rate of change in the RVP (dP/dt) following depolarization of the right ventricle. The test AV delay interval providing the lowest amplitude RVP at the peak dP/dt, indicating the lowest pulmonary blood pressure, is selected as the optimal AV delay. The system may be fully contained in an implanted pacemaker system including a right ventricular absolute blood pressure sensor and automatically invoked to determine the optimum AV delay for the prevailing atrial heart rate at any time, or may be invoked at a predetermined time of day or may be invoked by a programmed-in command. The system may also be employed on a temporary basis in conjunction with an implanted dual chamber pacemaker and an external pacemaker programmer with a temporary absolute blood pressure sensor to provide the blood pressure signals.

28 Claims, 12 Drawing Sheets

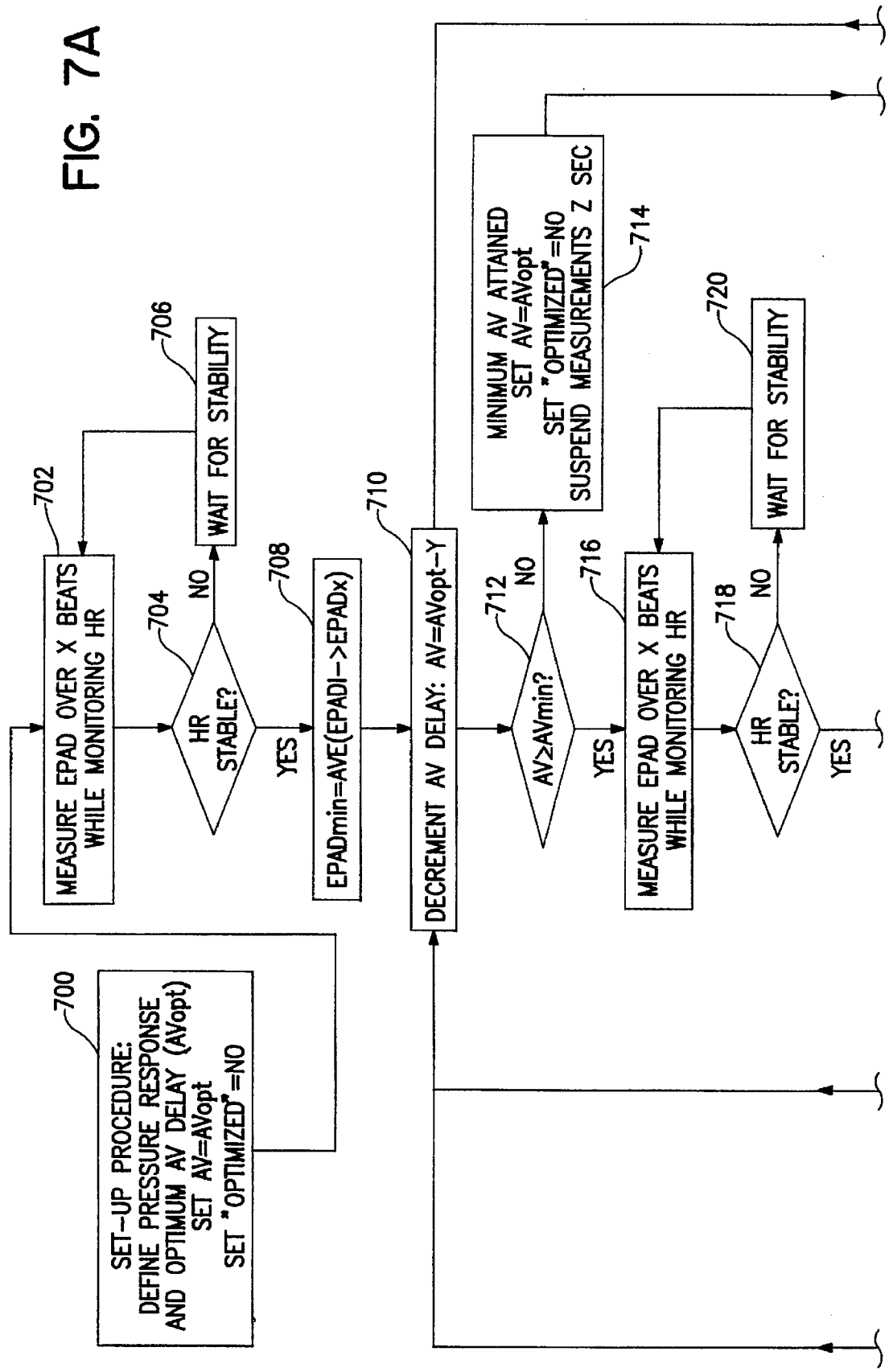

METHOD AND APPARATUS FOR OPTIMIZING PACEMAKER AV DELAY

FIELD OF THE INVENTION

The present invention relates to dual chamber cardiac pacemakers, including dual chamber, rate responsive cardiac pacemakers, and particularly to a method and apparatus for determining an atrioventficular (AV) delay interval to maintain optimal left heart AV mechanical synchrony and function.

BACKGROUND OF THE INVENTION

Dual chamber pacing modes, particularly, the multi-programmable, DDD pacing mode, have been widely adopted for pacing therapy. This mode has a sensor augmented variant mode called "DDDR", where the "R" stands for rate-adaptive or rate modulation of the base or lower pacing rate as a function of a physiologic signal related to the need for cardiac output.

A DDD pacemaker includes an atrial sense amplifier to detect atrial depolarizations or P-waves, and a ventricular sense amplifier to detect ventricular depolarizations or R-waves. If the atrium of the heart fails to spontaneously beat within a predefined time interval (atrial escape interval), the pacemaker supplies an atrial pace pulse to the atrium through an appropriate lead system. Following an atrial event (either sensed or paced) and the expiration of an AV delay interval, the pacemaker supplies a ventricular pace pulse to the ventricle through an appropriate lead system, if the ventricle fails to depolarize on its own. Such AV synchronous pacemakers which perform this function have the capability of tracking the patient's natural sinus rhythm and preserving the hemodynamic contribution of the atrial contraction over a wide range of heart rates.

Many patients have an intact sinoatrial (SA) node that generates the atrial depolarizations detectable as P-waves, but inadequate AV conduction. For these patients, the DDD mode, which attempts to pace the ventricles in synchrony with the atria, is generally adequate for their needs. Patients with Sick Sinus Syndrome (SSS) have an atrial rate which can be sometimes appropriate, sometimes too fast, and sometimes too slow. For SSS patients, the DDDR mode provides some relief by pacing the atria and ventricles at a physiologic rate determined by a sensor which senses a physiological indicator of the patient's metabolic needs. DDDR pacemakers employing sensed cardiac impedance or pressure related parameters to derive a sensor related pacing rate include U.S. Pat. Nos. 4,566,456, 4,730,619, 4,899,751, 4,899,752, 4,936,304, 5,003,976, 5,163,429 and 5,330,511.

In DDDR pacing for SSS patients, reliance on the intrinsic atrial rate is preferred if it is appropriately within an upper rate limit and a lower rate limit. At times when the intrinsic atrial rate is inappropriately high or low, a variety of "mode switching" schemes for effecting switching between the DDD and DDDR modes (and a variety of transitional modes) based on the relationship between the atrial rate and the sensor derived pacing rate have been proposed as exemplified by commonly assigned U.S. Pat. No. 5,144,949, incorporated herein by reference.

Typically, the AV delay interval in such DDD and DDDR pacemakers is either fixed or varies with the prevailing spontaneous atrial rate, measured as an interval, or sensor derived atrial escape interval corresponding to the sensor derived atrial pacing rate. The variation of the AV delay as a function of the atrial escape interval in early AV synchronous pacemakers is disclosed, for example, in U.S. Pat. No. 4,108,148. The variation of the AV interval as a function of a sensed physiologic signal or an atrial escape interval pacing rate derived therefrom is disclosed in the above-referenced '511 patent and in U.S. Pat. Nos. 4,303,075 and 5,024,222.

The maintenance of AV mechanical synchrony is of vital importance in patients with compromised cardiac function, including hypertrophic cardiomyopathy, dilated cardiomyopathy, hypertensive heart disease, restrictive cardiomyopathy, congestive heart failure and other disorders that are characterized by significant diastolic dysfunction. In such patients, passive ventricular filling is reduced due to poor ventricular compliance and incomplete or delayed relaxation. Consequently, there is increased reliance on atrial contraction for ventricular filling sufficient to achieve adequate stroke volume and maintain low atrial and pulmonary pressure.

In addition, a loss of AV electrical and mechanical synchrony can result in series of asynchronous atrial and ventricular depolarizations at independent rates that periodically result in an atrial depolarization that closely follows a ventricular depolarization. When this occurs, the left atrium contracts against a closed mitral valve, resulting in impeded venous return from the pulmonary vasculature due to increased atrial pressure and possibly even retrograde blood flow into the pulmonary venous circulation. As a result, the volume and pressure in the pulmonary venous circulation rise. Increased pulmonary pressures may lead to pulmonary congestion and dyspnea. Distention of the pulmonary vasculature may be associated with peripheral vasodilation and hypotension. In addition, the concomitant atrial distention is associated with increased production of atrial natriuretic factor and increases the susceptibility to atrial arrhythmias and possibly rupture of the atrial wall. Finally, turbulence and stagnation of blood within the atrium increase the risk of thrombus formation and subsequent arterial embolization. Restoration of AV mechanical synchrony would be expected to reverse these deficits.

Theoretically, AV synchrony is maintained during dual chamber cardiac pacing by setting the AV delay interval in a physiological range related to the spontaneous atrial rate or the sensor derived rate, depending on which is the controlling pacing mode, as described above. However, while "physiological" AV delays may ensure right heart AV electrical synchrony, in patients with significant interatrial and/ or interventricular conduction delays, left heart electrical and mechanical synchrony, and thus hemodynamic performance, may be significantly compromised. The monitoring of left heart AV mechanical synchrony during pacemaker programming could aid in establishing the optimal pacemaker AV delay for peak hemodynamic performance. Likewise, incorporation of such monitoring capability into a pacemaker device could permit continuous adjustment of the pacemaker AV delay to maintain optimal left heart AV mechanical synchrony and function. However, due to the high left heart pressure and the risk of tamponade and thromboembolism, pacing leads and sensor probes cannot readily be placed in or on the left heart.

Under steady state conditions, a loss of left heart AV mechanical synchrony may be expected to produce an increase in pulmonary capillary wedge pressure and pulmonary artery systolic and diastolic pressure. Therefore, a sensor capable of detecting such changes could be used as a monitor for steady state changes in left heart AV mechanical synchrony. Initial feasibility studies have been performed in which pulmonary vascular pressure was monitored by a sensor lead chronically positioned in the pulmonary artery as described by Steinhaus et at., in "Initial Experience with an Implantable Hemodynamic Monitor" *Circulation*, vol. 93, no. 4, Feb., 1996, pp. 745-52. More recently, it has been reported that a right ventricular absolute pressure sensor, being developed by the assignee of the present invention, can be used to derive an estimated Pulmonary Artery Diastolic (EPAD) and pulmonary capillary wedge pressure as described by Ohlsson et al, in "Monitoring of Pulmonary Arterial Diastolic Pressure Through a Right Ventricular Pressure Transducer", *Journal of Cardiac Failure*, vol. 1, no. 2, 1995, pp. 161-168 and by Reynolds et al., in "Measurement of Pulmonary Artery Diastolic Pressure From the Right Ventricle", *JACC*, vol. 25, no. 5, Apr., 1995; 1176-82. An implantable system for providing such monitoring is disclosed in commonly assigned U.S. Pat. No. 5,368,040. An absolute pressure sensor and circuitry for developing an absolute right ventricular or other heart chamber or vessel pressure signal is described in detail in commonly assigned U.S. patent application Ser. No. 08/394,870 filed Feb. 2, 1996, for IMPLANTABLE CAPACITIVE ABSOLUTE PRESSURE AND TEMPERATURE SENSOR and Ser. No. 08/394,860 filed Feb. 2, 1996, for IMPLANTABLE CAPACITIVE ABSOLUTE PRESSURE AND TEMPERATURE MONITORING SYSTEM.

SUMMARY OF THE INVENTION

Accordingly, the present invention is directed to a system for optimizing the AV delay interval of an AV synchronous pacing regimen to obtain optimal right and left atrial mechanical synchrony to the extent possible even in those patient hearts exhibiting mitral valve insufficiency.

The present invention incorporates an AV delay interval optimization system for establishing an optimum AV delay interval for optimal left heart AV mechanical synchrony and function operable in conjunction with an AV synchronous pacemaker pulse generator comprising the method steps of and means for: (a) determining a stable atrial heart rate; (b) on determination of a stable heart rate in step (a), continuing with steps (c)-(i) with an initial test AV delay interval; (c) in the time period following a ventricular pace pulse delivered at the end of the initial test AV delay interval, measuring right ventricular blood pressure and providing a right ventricular pressure (RVP) signal; (d) deriving a pressure rate of change signal (dP/dt) from the measured RVP signal; (e) determining a peak amplitude of the dP/dt signal; (f) measuring the RVP signal amplitude at the determined peak dP/dt signal as an estimated Pulmonary Artery Diastolic (EPAD) pressure; (g) repeating steps (c)-(f) while a stable atrial heart rate continues with a set of adjusted test AV delay intervals changed by a predetermined delta value between a minimum and a maximum AV delay interval to derive a set of EPAD pressure values; (h) identifying the test AV delay interval providing the lowest amplitude EPAD pressure value; and (i) selecting the identified test AV delay interval as the AV delay interval employed in the A-V synchronous pacing method.

The present invention is preferably implemented into a dual chamber pacemaker of the type operating in accordance with an AV synchronous pacing method comprising the steps of and means for: timing a V-A pacing escape interval from a paced ventricular event; delivering an atrial pace pulse to an atrium of a patient's heart at the time out of the V-A pacing escape interval unless an atrial sensed event occurs within the pacing escape interval; prematurely terminating the V-A pacing escape interval on the sensing of an atrial sensed event within the V-A pacing escape interval; timing an AV delay interval starting from a sensed atrial event or delivery of an atrial pace pulse; delivering a ventricular pace pulse to a ventricle of the patient's heart at the termination of the AV delay interval unless a ventricular sensed event occurs within the AV delay interval; prematurely terminating the AV delay interval on the sensing of a ventricular sensed event within the AV delay interval; and restarting the V-A pacing escape interval on a ventricular pace pulse or a ventricular sensed event.

The optimization method and apparatus preferably operates from time to time in the implanted pacemaker when the atrial rate is regular for a predetermined time period or at predetermined times of day. Alternatively or additionally, the pacing system in which the optimization method and apparatus are preferably implemented further comprises the steps of and means for programming operating modes thereof in response to programmed-in commands from an external programmer, and the optimization method and apparatus is preferably initiated with a programmed-in command from the external pacemaker programmer.

In a preferred embodiment, the pacemaker pulse generator comprises downlink telemetry means responsive to programmed-in commands from an external programmer, and the optimization system further comprises the means for and step of initiating the optimization method with a programmed-in command from the external pacemaker programmer; and selecting the maximum and minimum test AV delay intervals in response to programmed in commands from the external pacemaker programmer to provide a wide range of absolute pressure measurements to distinguish local minimum pressure values from true minimum pressure values among the plurality of absolute pressure values.

In a further variation, the pacemaker pulse generator comprises means for providing uplink telemetry of the test AV delay intervals and the measured absolute blood pressure levels to the external programmer; and the external programmer further comprises means for displaying the telemetered absolute pressure values in relation to the range of test AV delay intervals.

The optimized AV delay intervals may be stored in pacemaker memory for use in association with an intrinsic or paced atrial heart rate until the optimized AV delay interval is replaced. In the preferred embodiment of the device, the initialization procedure comprises measuring intrinsic A-V conduction times following both delivered atrial pacing pulses and sensed atrial depolarizations, which measurements are employed to define two differing AV escape intervals for the pacemaker, following sensed and paced events.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
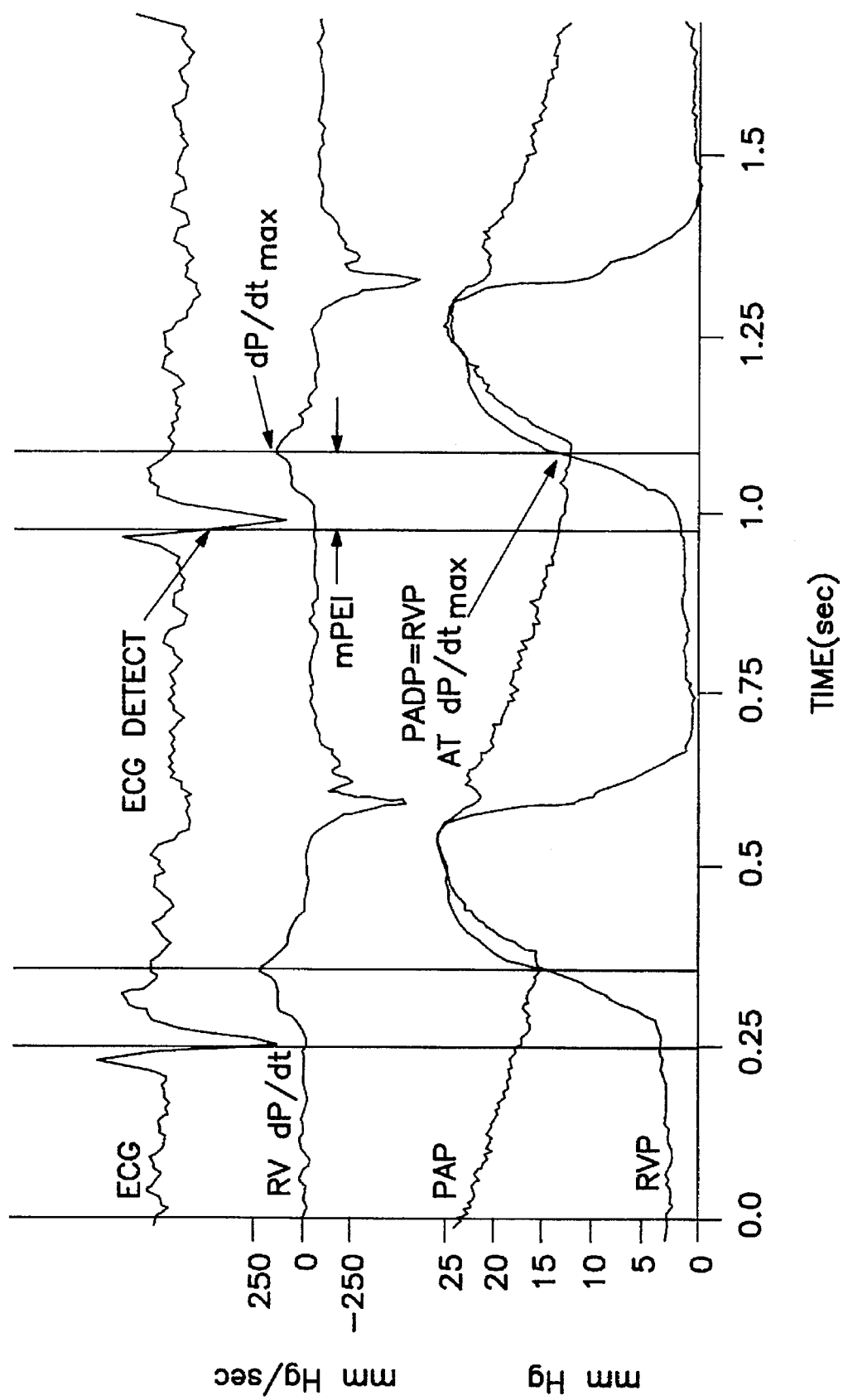
FIG. 1 is a depiction of the cardiac cycle attendant depolarization of the heart chambers and attendant ventricular and pulmonary blood pressure waves.
Figure 2:
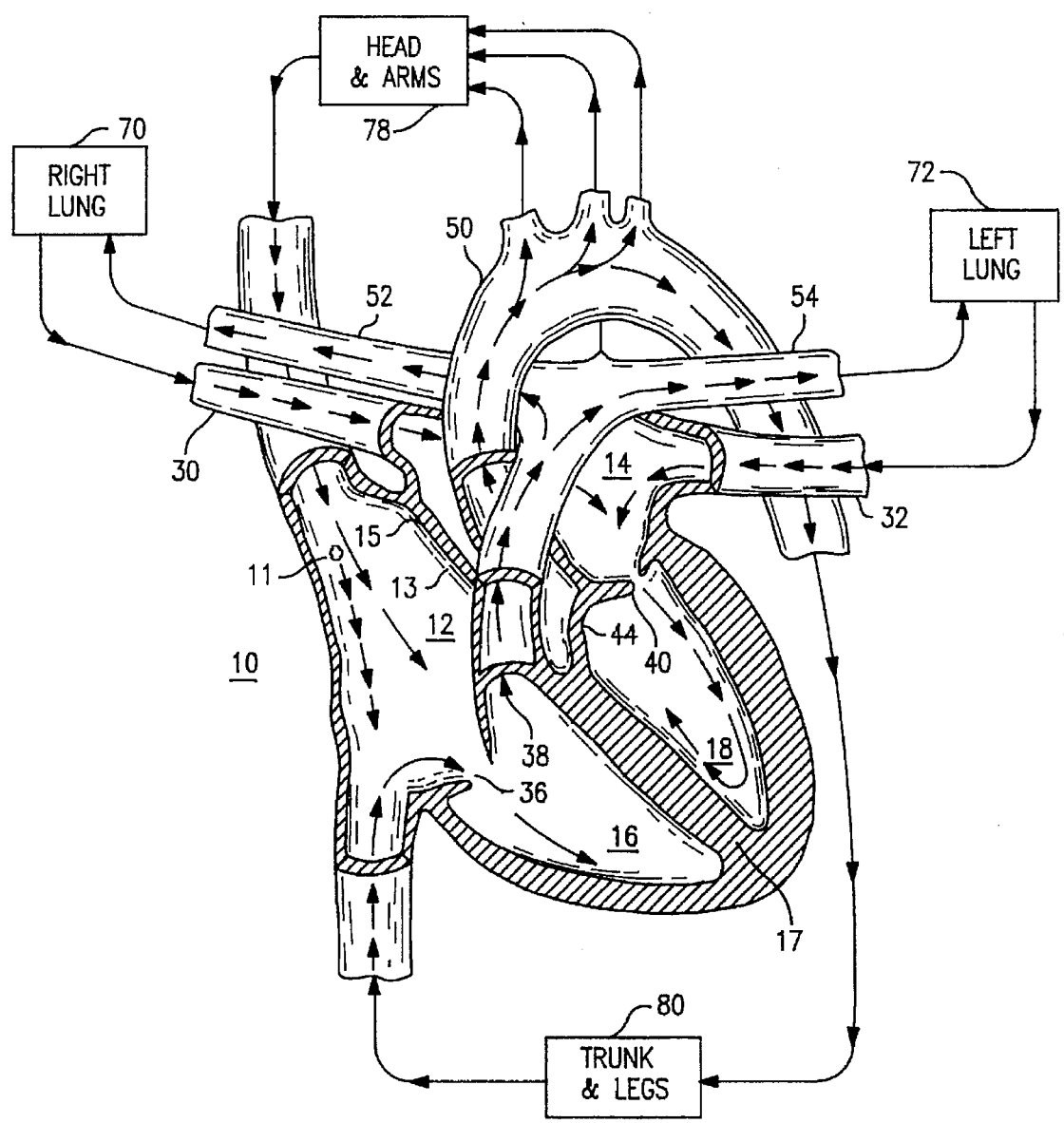
FIG. 2 is a view of the chambers of the heart and the cardiac vessels in the circulatory system during contraction of the atria in an atrial depolarization to fill the ventricles with blood pooled in the atria from the circulatory system.
Figure 3:
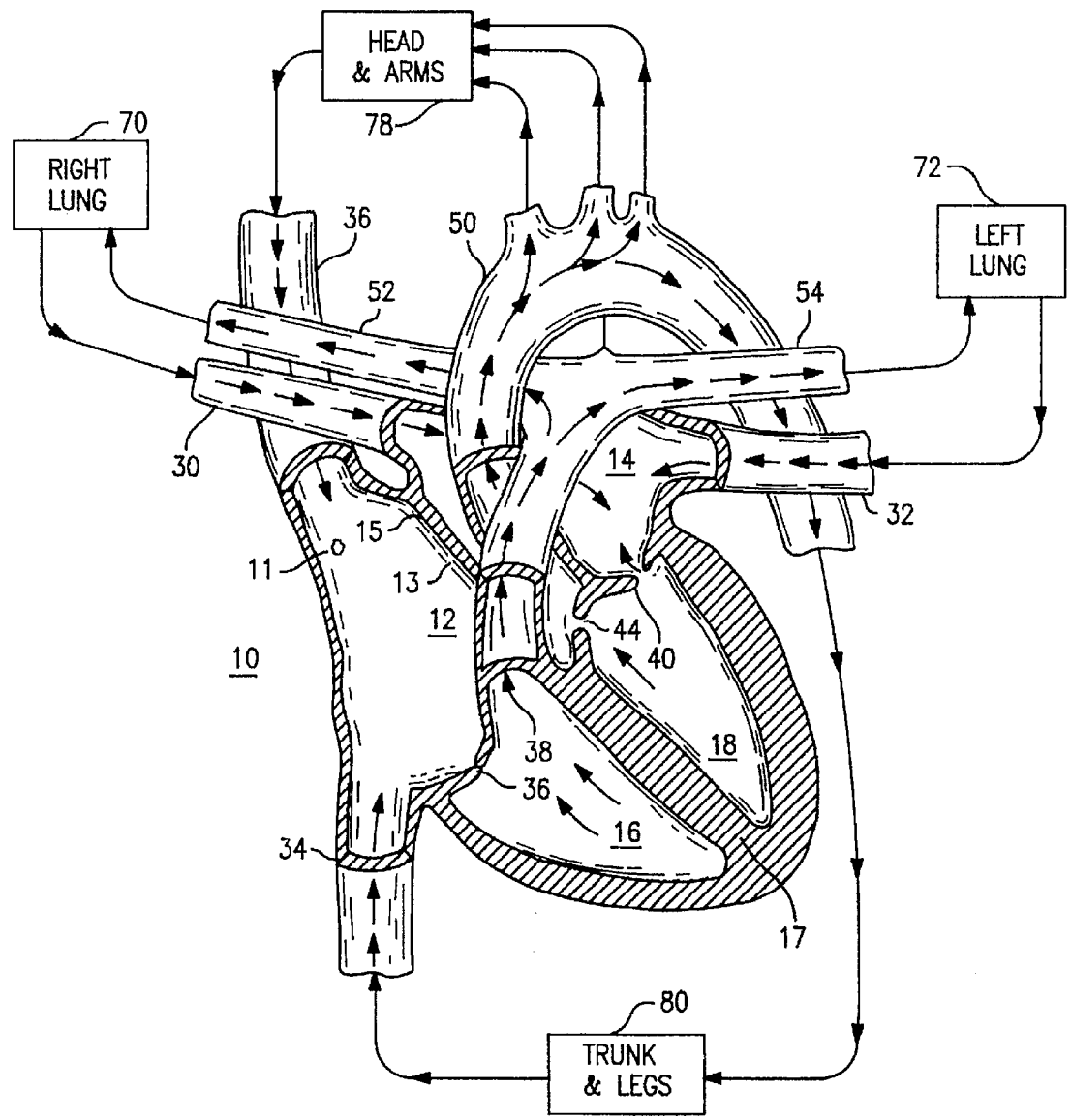
FIG. 3 is a view of the chambers of the heart and the cardiac vessels in the circulatory system during contraction of the ventricles to expel blood into the circulatory system.

Before describing the inventive method and apparatus embodied in one preferred system, attention is directed to FIGS. 1–3 that depict the cardiac circulatory system and synchronized depolarizations of the heart chambers in a patient suffering from mitral valve insufficiency, for example, that can lead to elevated pulmonary pressure. In FIG. 1, the ECG waveform exhibits the characteristic PQRST electrical depolarization waves attendant a ventricular heart cycle or beat. The ECG waveform is depicted in relation to the fluctuations in absolute pressure in the right ventricle (RVP) and the pulmonary artery (PAP) and in relation to a right ventricular dP/dt signal. The pressure signals are taken from pressure sensors located in the right ventricle and the pulmonary artery as described in the above-referenced Reynolds et al. paper. FIGS. 2 and 3 schematically depict the contractions of the atria and the ventricles in the heart cycle correlated to the P-wave and the QRST complex in FIG. 1.

In this regard, FIG. 2 is a schematic view of the chambers of the heart 10 and the cardiac vessels in the circulatory system during a normal contraction of the right and left atria 12 and 14 in an atrial depolarization propagated from the SA node 11 and detected as the P-wave in FIG. 1. In FIG. 2, the atrial depoladzation propagates through the walls of the right and left atria 12 and 14 and toward the AV node 13 above the junction of the atrial septum 15 separating the atrial chambers and the ventricular septum 17 separating the ventricular chambers. The S-A node 11 is located high in the right atrial wall and is influenced by nerve fibers from the autonomic nervous system to depolarize at a rate correlated to the need for cardiac output.

The contraction of the atria 12 and 14 fills the right and left ventricles 16 and 18 with blood previously pooled in the atrial chambers 12 and 14 from the circulatory system. Venous return blood from the lower and upper body enters the right atrium 12 through the inferior vena cava 34 and the superior vena cava 36. Oxygenated blood returns from the right and left pulmonary veins 30 and 32 from the right and left lungs 70 and 72, respectively. During the contraction of the right atrium 12, the pooled venous blood enters the right ventricle 16 through the tricuspid valve 36. After a short delay related to the propagation of the atrial depolarization into the left atrium 14, oxygenated blood enters the left ventricle 18 through the mitral valve 40. The pulmonary valve 38 and the aortic valve 44 remain closed as the relaxed ventricles 16 and 18 fill with blood ejected from the atria 12 and 14, respectively.

After the A-V conduction time, the right and left ventricles 16, 18 contract forcing venous blood from the right ventricle 16 through the pulmonary valve 38 into the right and left pulmonary artery branches 52, 54 and oxygenated blood from the left ventricle through the aorta 50 for distribution into the branch arteries extending to the upper and lower body, head and limbs. In a healthy heart, the tricuspid valve 36 and the mitral valve 40 are closed during contraction of the right and left ventricles 16 and 18.

A cardiac cycle commencing with the synchronous contraction of the atria and ventricles is completed in following time interval during which the right and left atria 12 and 14 re-fill with venous and oxygenated blood, respectively. In sinus rhythm, the interval between sequential intrinsic atrial (P-P) or ventricular (R-R) depolarizations may be on the order of 400.0 ms to 1,000.0 ms for a corresponding sinus heart rate of 150 bpm to 60 bpm, respectively. In the absence of valve disease or dissociation between atrial and ventricular depolarizations, the cardiac valves function properly, and average pulmonary blood pressure and cardiac filing pressure are optimized for efficient blood gas exchange and heart function.

However, in the absence of proper AV synchrony or in the presence of a diseased mitral valve, these pressures can either rise or fall to average levels that can be symptomatic. For example, it will be assumed that the mitral valve 40 is diseased or otherwise incompetent or defective, and that the valve leaflets fail to fully close in response to the contraction of the ventricles 16 and 18, as depicted in FIG. 3. In FIG. 3, the ventricles 16 and 18 contract a short AV conduction time later after the electrical signal is propagated down the His-Purkinjie fiber system in the ventricular septum 17. The contractions of the right and left ventricles 16 and 18 force closed the tricuspid valve 36 and the mitral valve 40 while forcing open the pulmonary valve 38 and aortic valve 44. The QRS depolarization, or R-wave, represents the synchronous depolarization wave and attendant mechanical contraction of the ventricular myocardial cells, and the following T-wave accompanies the repolarization and attendant relaxation of the ventricular myocardial cells of the ventricles 16 and 18. Venous blood is propelled by the forceful contraction of the right ventricle 16 through the right and left pulmonary artery branches 52 and 54 of the pulmonary artery and into the lungs 70 and 72. Oxygenated blood is propelled through the open aortic valve 44 and the aorta to vessels in the head and arms 78 and trunk and legs 80.

Because of the insufficient closure of the mitral valve, 40, however, oxygenated blood also is ejected from the left ventricle back into the left atrium 14. This pressurized blood elevates the pressure in the left atrium 14 which is reflected back into the pulmonary system. The elevated pulmonary blood pressure can cause the patient to suffer from congestion or pulmonary edema resulting in labored breathing (i.e., dyspnea, orthopnea) A typical treatment for such a patient involves medications to relieve pulmonary congestion or surgical valve repair or replacement. These symptoms are not necessarily correlated to the need for cardiac pacing. However, these problems may be exacerbated by impaired AV synchrony and could be minimized by optimally timed cardiac pacing.

In the blood pressure diagrams of FIG. 1, it may be observed that the pulmonary blood pressure PAP and the right ventricular blood pressure RVP changes track and lag behind the peak R-waves of the cardiac cycles. The peak of the RVP signal is referred to as the Peak RV systolic pressure, and the baseline RVP pressure between peaks is the referred to as the diastolic pressure. The amount of blood filling the atria 12 and 14 depends in part on the stiffness of the atrial chambers and is a function of the atrial distending pressure, i.e., the difference between the atrial blood pressure and the pleural pressure of the pleural cavity surrounding the heart. At the end of diastole, when atrial blood has stopped passively filling the ventricles, the ventricular diastolic pressure equals the atrial pressure. During the depolarizations of the atria 12, 14, and the ventricles 16, 18, they also contract in size as systolic blood pressure increases.

As described in the above-referenced articles, and in reference to FIG. 1, the PAP decays slowly from its peak over the cardiac cycle. The PAP is determined by the rate of blood flow into the pulmonary artery from the right ventricle and the rate of blood flow out into the pulmonary capillaries and from the venous system into the left atrium. Factors that increase the former or retard the latter, e.g. mitral valve regurgitation, increase the average PAP over the heart cycle.

Specifically, upon contraction of the right ventricle 16 and closure of the tricuspid valve 36, RVP rises relatively rapidly but then becomes equal with the decaying PAP when the pulmonary valve 38 opens. As the above-referenced papers point out, the opening of the pulmonary valve 38 slows the increase in the pressure rate of change in RVP, and both the PAP and RVP increase thereafter at the same rate to the systolic peak pressure. The point in the cardiac cycle at which this rate of change in the increase occurs due to opening of the pulmonary valve 38 can be detected from the positive dP/dt signal peak ($dP/dt^{peak}$). In reference to FIG. 1, it can be seen that the RVP approximates the diastolic PAP at this point. Thus, the PAP in the pulmonary artery branches 52, 54 at the $dP/dt^{peak}$ can be estimated by the RVP at the same instant and is herein referred to as the EPAD pressure. In normal hearts, the EPAD value may be on the order of the 15–20 mm Hg range as depicted in FIG. 1. The EPAD value may be 25–50% greater than normal in a patient with poor AV synchrony or a defective mitral valve 40 that regurgitates blood back into the left atrium if the left ventricle contracts while the mitral valve is not fully closed.

In accordance with the present invention, it is realized that the EPAD can be monitored and employed to establish an AV interval in atrial synchronous pacemakers, particularly DDD or DDDR pacemakers, that optimizes left heart AV synchrony and minimizes the possibility that the triggered ventricular depolarization occurs at an inappropriate time with respect to the atrial depolarization. Moreover, in patient's suffering from mitral valve insufficiency, an optimal AV delay can be selected that at least does not exacerbate the pulmonary pressure. In a pacemaker dependent patient with a defectively functioning mitral valve 40, synchronously pacing the right ventricle at a certain optimum AV delay interval will allow the PAP to at least not be further elevated by an ill-timed depolarization of the ventricles.

Figure 4:
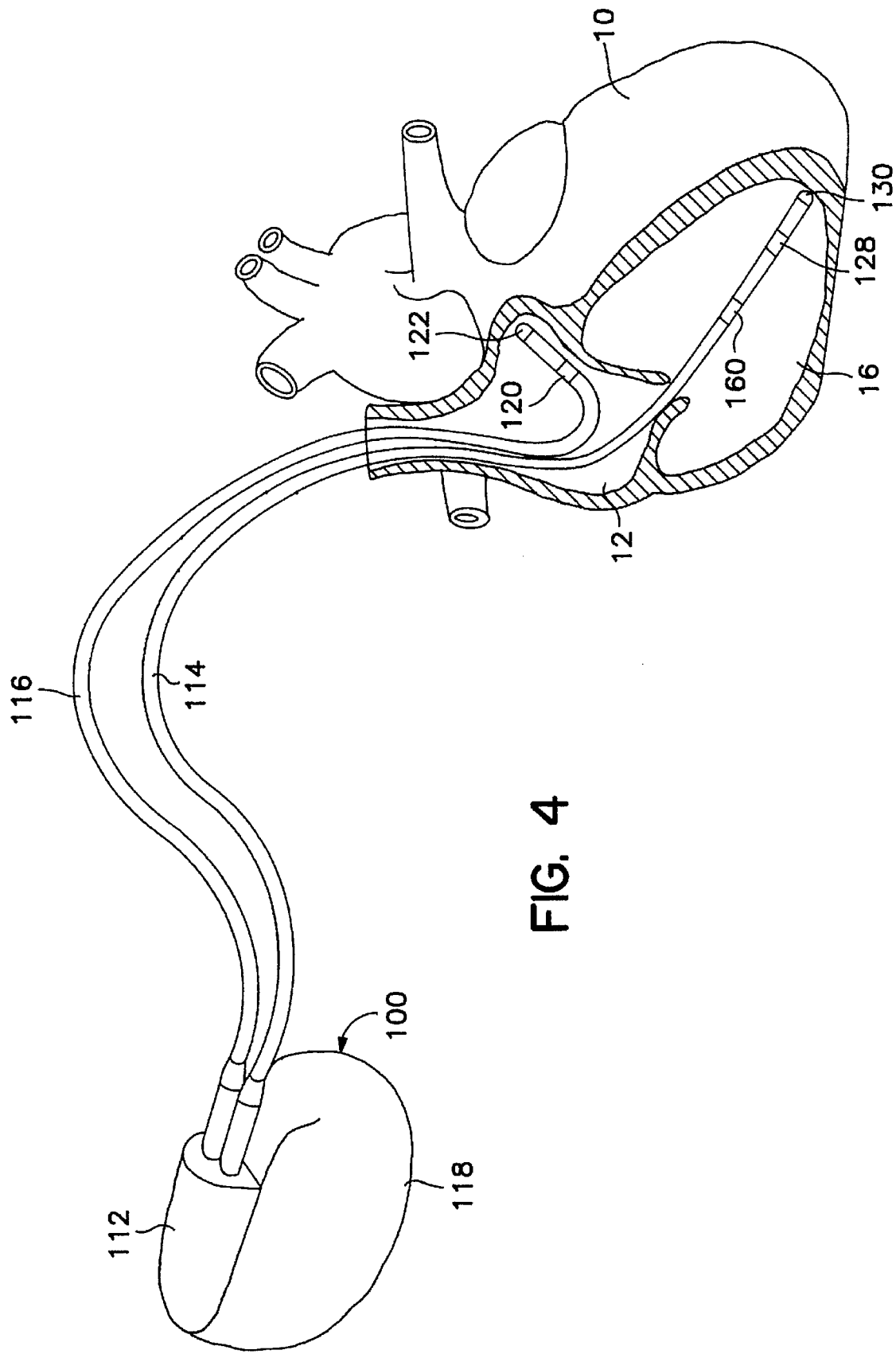
FIG. 4 is a schematic illustration of a dual chamber pacemaker in which the present invention may be implemented.

Turning now to FIG. 4, it depicts the external configuration of a dual chamber IPG 100, which is provided with a hermetically sealed enclosure 118, typically fabricated of biocompatible metal such as titanium. Mounted to the top of the enclosure 118 is a connector block assembly 112, which receives electrical connectors located on the proximal ends of unipolar or bipolar leads 114 and 116 (bipolar leads are depicted). The combination of the leads 114 and 116 and the IPG 100 constitute an implantable dual chamber pacemaker, e.g. a DDD or DDDR pacemaker Lead 116 is an atrial bipolar pacing lead, carrying two electrodes 120 and 122. Electrodes 120 and 122 are used both to sense atrial depolarizations (P-waves) and to deliver atrial pacing pulses. Atrial pacing pulses may be delivered between electrodes 120 and 122 in a bipolar pacing mode or between electrode 122 and the housing 118 of the IPG 100 in a unipolar pacing mode. Sensing of P-waves may occur between electrode 120 and electrode 122 in a bipolar sensing mode or between either of electrode 120 and 122 and the housing 118 of the IPG 100 in a unipolar sensing mode.

Similarly, lead 114 represents a ventricular bipolar pacing lead, carrying two electrodes 128 and 130. As discussed above in conjunction with atrial lead 116, electrodes 128 and 130 are used to sense and pace the ventricle. Bipolar ventricular pacing may be accomplished between electrodes 130 and 128 or unipolar ventricular pacing may be accomplished between electrode 130 and the conductive housing 118. Sensing of ventricular depolarizations or R-waves may be accomplished between electrodes 130 and 128 in a bipolar sensing mode or between either of electrodes 130 and 128 and the housing 118 of the IPG 26 in a unipolar sensing mode.

In accordance with one preferred embodiment of the invention, an absolute pressure sensor 160 is incorporated into the body of ventricular pacing lead 114 proximal to the ring electrode 128. Absolute pressure sensor 160 is preferably a capacitive absolute pressure sensor of the type described in the above referenced Ser. No. 08/394,870 application. Capacitive absolute pressure sensor 160 may alternatively be provided at the distal end of a further lead body and separately coupled to connector block assembly 112.

The preferred embodiment of the IPG 100 preferably operates in a DDD or DDDR pacing mode, wherein pacing pulses are delivered to both right atrium 12 and right ventricle 16 in AV synchrony, and wherein sensed atrial and ventricular depolarizations are both effective to inhibit delivery of the next scheduled pacing pulse in the chamber in which they are detected or in any related mode where the AV delay interval is employed, including the related VDD, DDI, DVI, DVIR and DDIR modes. The AV delay optimization provided by the determination of the lowest value of the EPAD afforded by the present invention is believed optimally practiced in a pacemaker operating in such modes.

Figure 5:
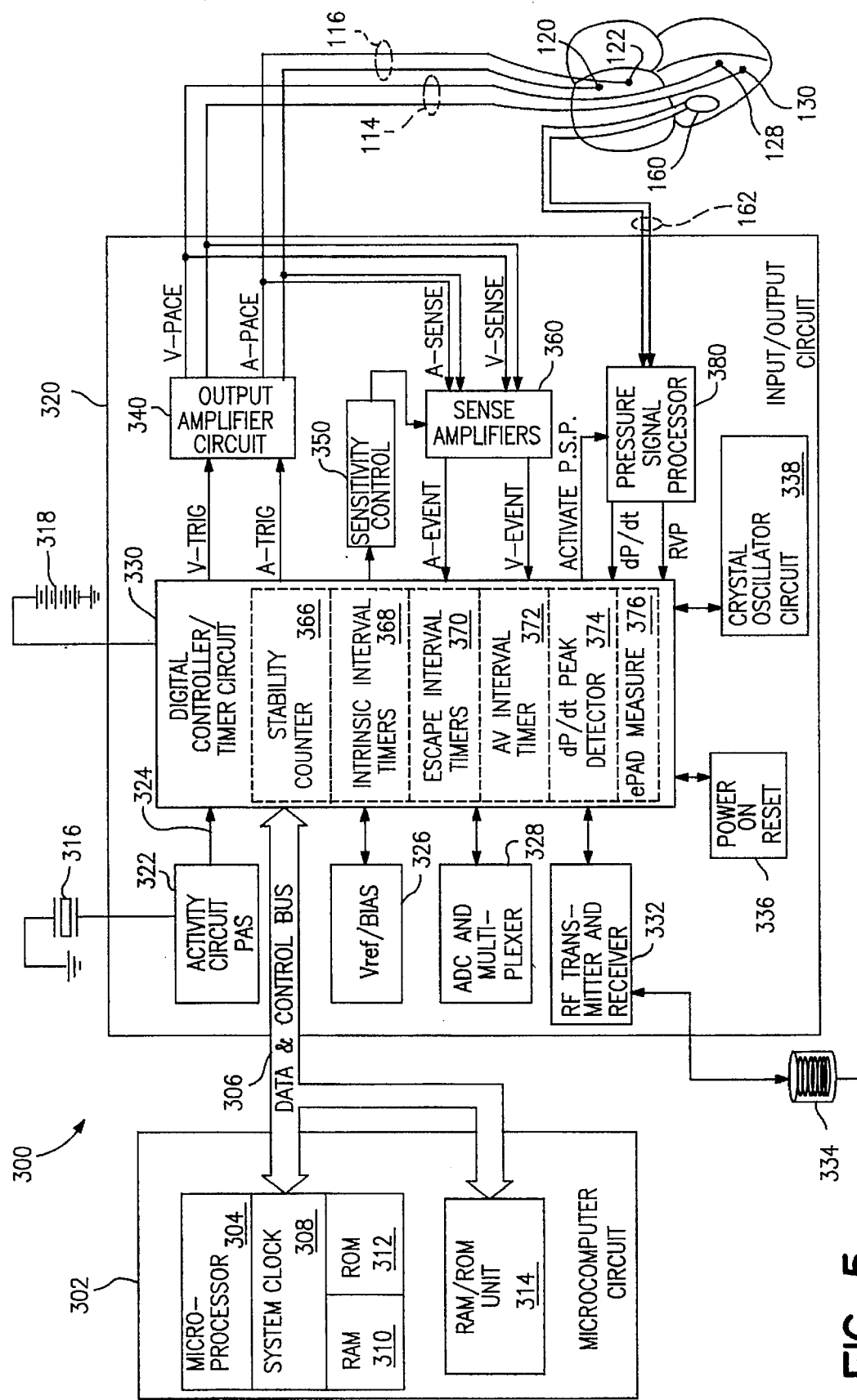
FIG. 5 is a block diagram of an exemplary DDDR IPG used in the dual chamber pacemaker of FIG. 4 in which the invention may be practiced.

Turning now to FIG. 5, it depicts an IPG circuit 300 and atrial and ventricular lead system 114, 116 having programmable modes and parameters and a telemetry transceiver of a DDDR type known in the pacing art. The IPG circuit 300 is divided generally into a microcomputer circuit 302 and a pacing circuit 320. The pacing circuit 320 includes the output amplifier circuit 340 and the sense amplifier circuit 360, as well as a pressure signal processor 380 and a number of other components described below. The output circuit 340 and sense amplifier circuit 360 may contain pulse generators and sense amplifiers corresponding to any of those presently employed in commercially marketed cardiac pacemakers for atrial and ventricular pacing and sensing.

The bipolar leads 114 and 116 are illustrated schematically with their associated electrode sets 120, 122 and 128, 130, respectively, as coupled directly to the input/output circuit 320. Similarly, the right ventricular absolute pressure sensor 160 is schematically shown in the right ventricle 16 at the end of a further lead conductor pair 162 (that may or may not be incorporated into ventricular lead 114) and shown directly connected to the pressure signal processor 380. However, in the actual implantable device they would, of course, be coupled by means of removable electrical connectors inserted in connector block assembly 112, of FIG. 4.

Atrial depolarizations or P-waves in the A-SENSE signal that are sensed by the atrial sense amplifier result in an A-EVENT signal that is communicated to the digital controller/timer circuit 330. Similarly, ventricular depolarizations or R-waves in the V-SENSE signal are sensed by the ventricular sense amplifier result in a V-EVENT signal that is communicated to the digital controller/timer circuit 330. The EPAD signal is conducted to the pressure signal processor 380 which develops the RV dP/dt signal and the RVP signal shown in FIG. 1.

In order to trigger generation of a ventricular pacing or V-PACE pulse, digital controller/timer circuit 330 generates a V-TRIG signal at the end of an AV delay provided by AV delay interval timer 372. Similarly, in order to trigger an atrial pacing or A-PACE pulse, digital controller/timer circuit 330 generates an A-TRIG signal.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Data transmission to and from the external programmer of the patient communications control device of the present invention is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. The IPG transceiver system disclosed in commonly assigned U.S. patent application Ser. No. 08/584,851 filed Jan. 11, 1996, for ADAPTIVE, PERFORMANCE-OPTIMIZING COMMUNICATION SYSTEM may be employed to provide the uplink and downlink telemetry from and to the implanted medical device in the practice of the present invention.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-TRIG, V-TRIG, A-EVENT and V-EVENT signals. The specific values of the intervals defined are controlled by the microcomputer circuit 302 by means of data and control bus 306 from programmed-in parameter values and operating modes.

Control of timing and other functions within the pacing circuit 320 is provided by digital controller/timer circuit 330, operating under the general control of the microcomputer 302, which includes a set of timing and associated logic circuits of which certain ones pertinent to the present invention are depicted. The depicted timing circuits include a heart rate stability counter 366, an atrial interval timer 368 for timing elapsed V-A intervals, escape interval timers 370 for timing A-A, V-A, and/or V-V pacing escape intervals, and an AV delay interval timer 372 for timing an AV delay from a preceding A-EVENT (SAV) or A-TRIG (PAV). Microcomputer 302 controls the operational functions of digital controller/timer 324, specifying which timing intervals are employed, and setting at least the programmed-in base timing intervals, via data and control bus 306. Digital controller/timer circuit 330 starts and times out these intervals for controlling operation of the atrial and ventricular sense amplifiers in sense amplifier circuit 360 and the atrial and ventricular pace pulse generators in output amplifier circuit 340. Typically, digital controller/timer circuit 330 defines associated intervals including an atrial blanking interval following delivery of an A-TRIG pulse or V-TRIG pulse, during which atrial sensing is disabled, as well as ventricular blanking intervals following a V-TRIG atrial pulse, during which ventricular sensing is disabled. Digital controller/timer circuit 330 also defines an atrial refractory period (ARP) during which atrial sensing is disabled or the A-EVENT is ignored for the purpose of resetting the V-A escape interval. The ARP extends from the beginning of the SAV or PAV interval following either an A-EVENT or an A-TRIG and until a predetermined time following a V-EVENT or a V-TRIG as a post-ventricular atrial refractory period (PVARP). A ventricular refractory period (VRP) may also be timed out after a V-EVENT or V-TRIG. The durations of the ARP, PVARP and VRP may also be selected as a programmable parameter stored in the microcomputer 302. Digital controller/timer circuit 330 also controls sensitivity setting, of the atrial and ventricular sense amplifiers 360 by means of sensitivity control 350.

The activity sensor 316 is coupled to the implantable pulse generator housing 118 and may take the form of a piezoelectric crystal transducer as is well known in the art and its output signal is processed and used as a rate control parameter (RCP). If the IPG is programmed to a rate responsive mode, the patient's activity level developed in the patient activity circuit (PAS) 322 is monitored periodically, and the sensor derived V-A escape interval is adjusted proportionally. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

Alternatively or additionally, the dP/dt or the RVP signal provided by the pressure signal processor 380 may be used as the RCP alone or in conjunction with the activity signal to derive the pacing escape interval and related intervals. For example, the algorithms described in the commonly assigned U.S. Pat. Nos. 5,158,078, 5,154,170 and 5,282,839 may be so employed.

The microprocessor 304 also optionally defines a viable AV delay interval and variable ARPs and VRPs which vary with the escape interval established in response to the RCP(s) and/or in response to the intrinsic atrial rate. The variable AV delays are usually derived as a fraction of a maximum AV delay set for the pacing lower rate (i.e., the longest escape interval). In accordance with a first aspect of the present invention, the base AV delay can be optimized from a programmed-in value while the patient is resting and the intrinsic heart rate is at a stable and relatively low rate. In accordance with a second aspect of the invention, even if a variable AV delay that is defined based on the sensed atrial rate is used, any given variable AV delay value can also be optimized during any period of stable intrinsic atrial rhythm.

Figure 7B:
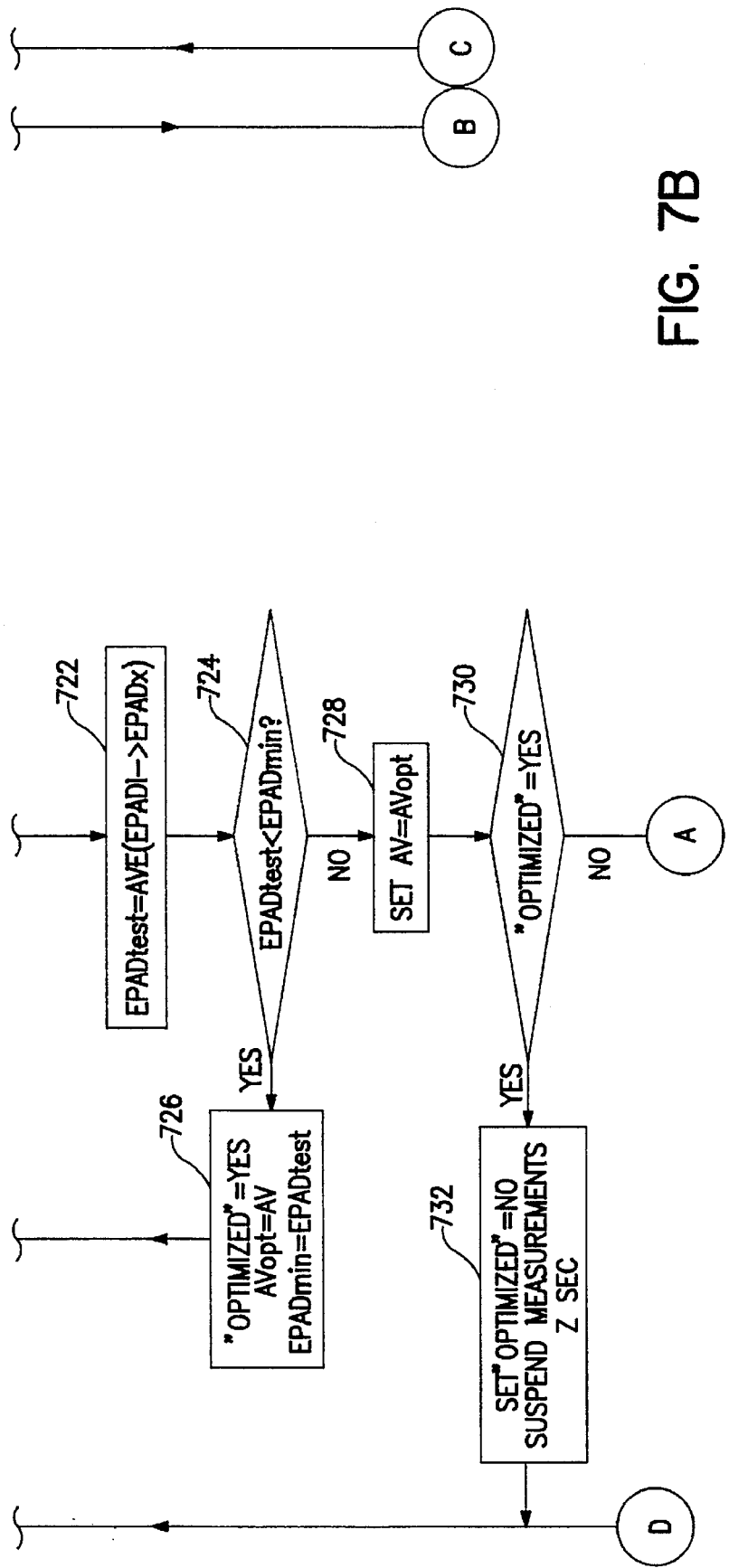
FIGS. 7 and 8 are a flow chart for carrying out the process steps and means for optimizing the AV delay interval in accordance with the invention.
Figure 8A:
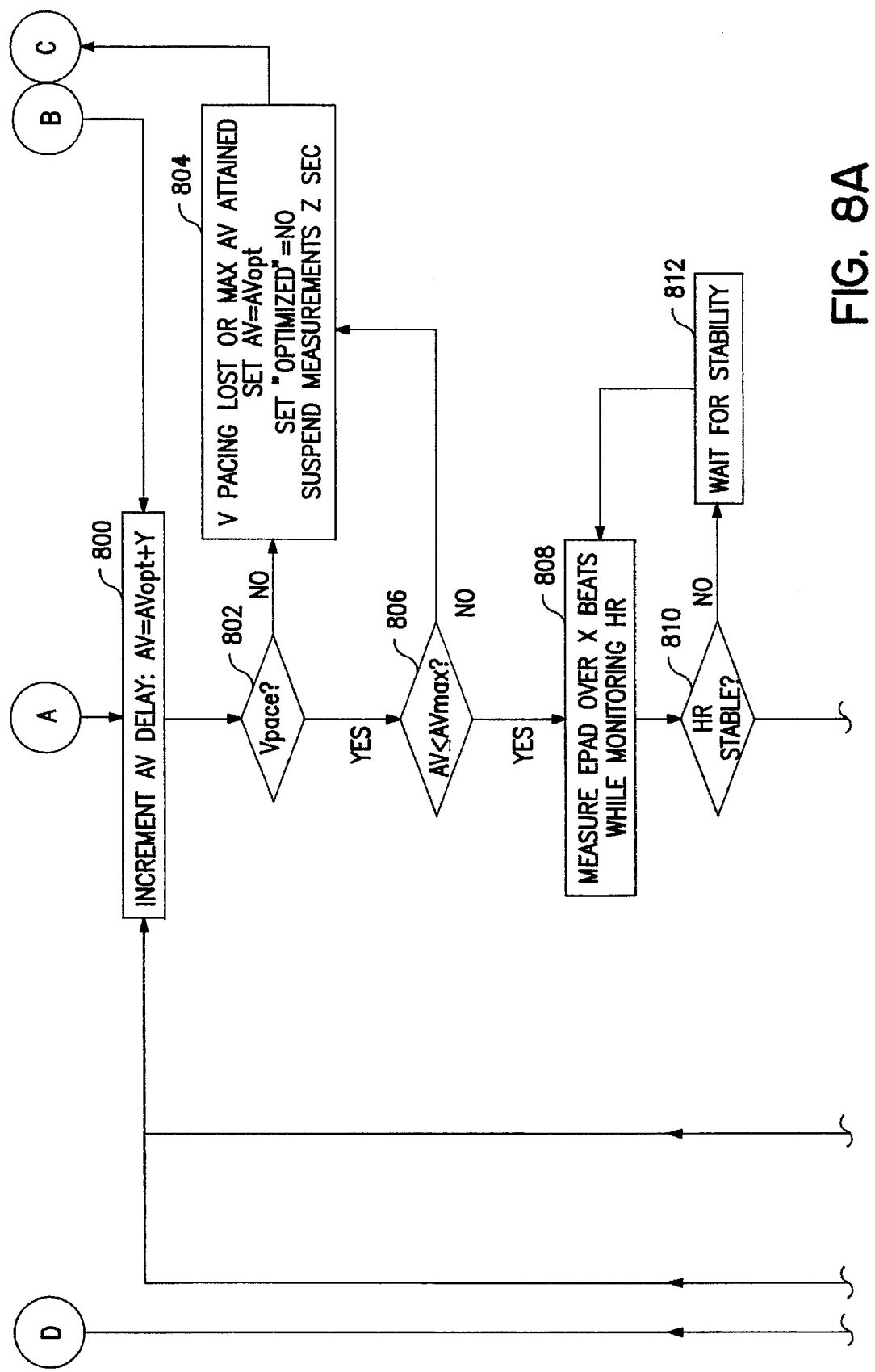
Figure 8B:
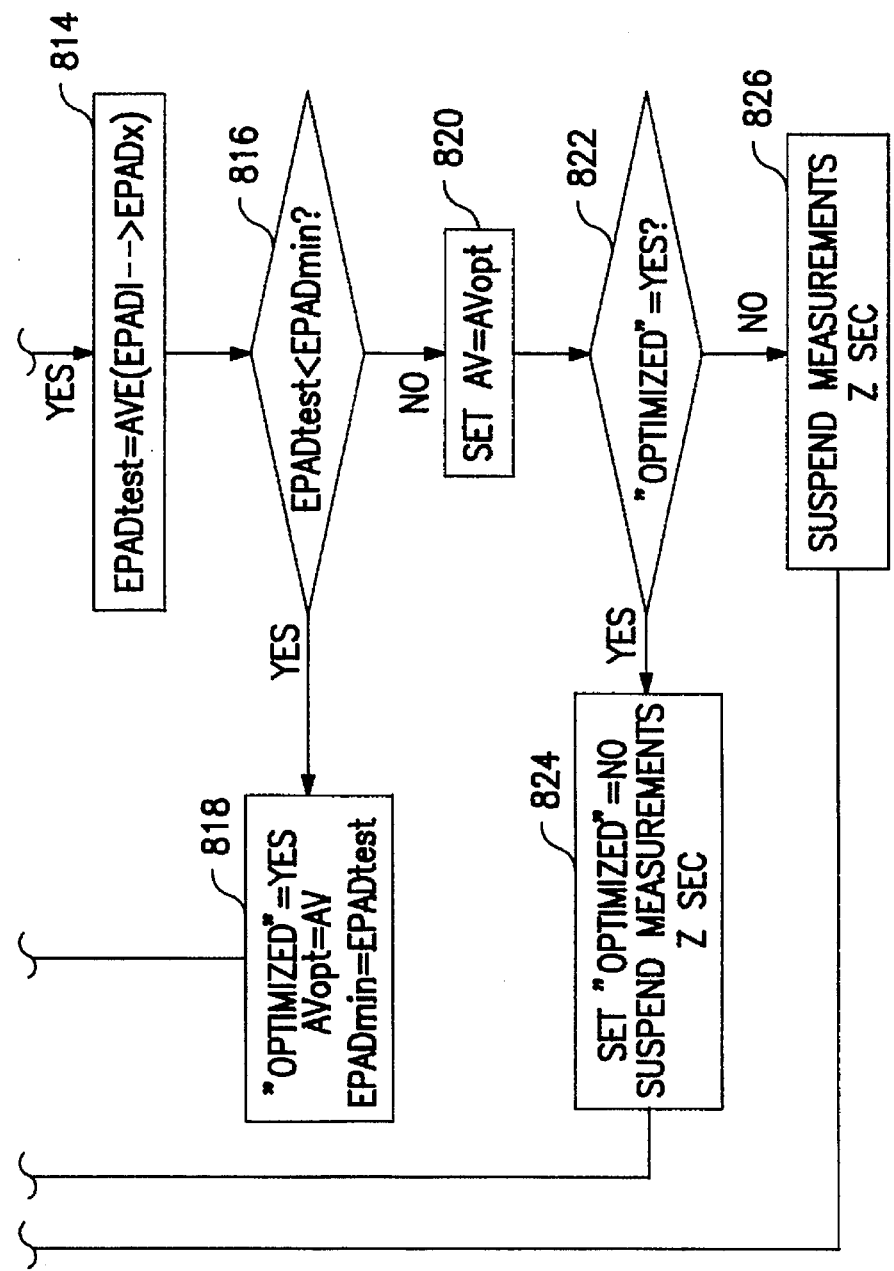

In regard to the derivation of the optimum AV delay interval in accordance with the present invention, when the algorithm depicted in the flow chart of FIGS. 7 and 8 is activated and certain conditions are met, the right ventricular pressure RVP is measured in the pressure signal processor 380 and supplied to the digital timer and controller circuit 330. In addition, pressure signal processor 380 processes the RVP signal to derive the dP/dt signal from the right ventricular pressure RVP and provides it to the digital timer/controller 330. A peak detector 374 in digital controller/timer circuit 330 determines the $dP/dt^{peak}$ and employs it to measure or sample the corresponding RVP signal amplitude and derive the EPAD value in the EPAD measure block 376. The EPAD signal amplitude is digitized in the ADC and multiplexor 328 and employed in the algorithm as described below. These functions of pressure signal processor 380 and a suitable circuit for providing the dP/dt and RVP signals are disclosed in detail in the above-referenced '040 patent. Circuitry which can power the absolute pressure sensor and provide a pressure output signal therefrom is disclosed in the above-referenced U.S. Ser. No. 08/394,860 patent application.

Figure 6:
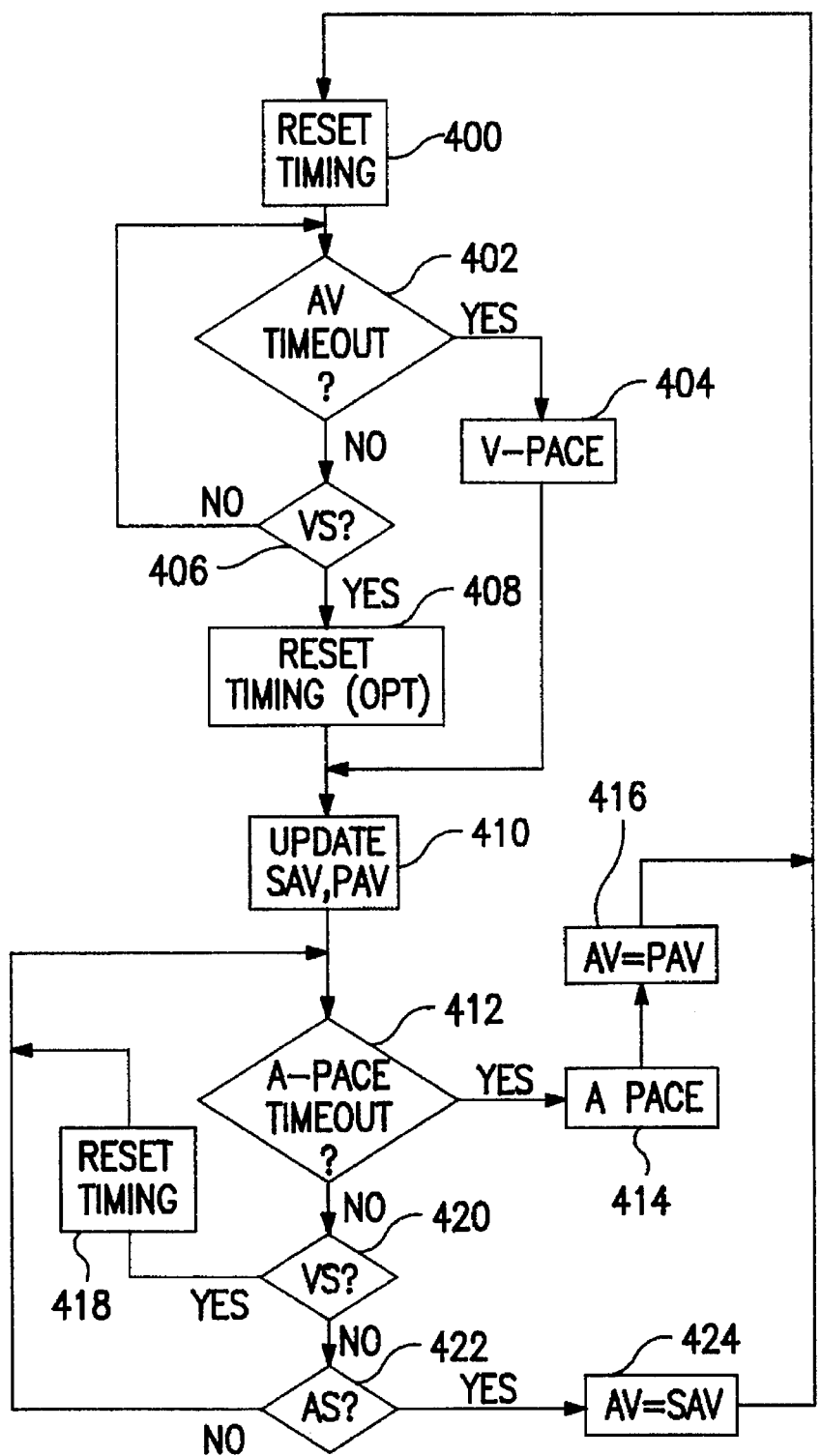
FIG. 6 is a flow chart of the overall timing of the DDDR pacemaker of FIGS. 4 and 5.

Before describing the algorithm for deriving the optimum AV delay interval to minimize pulmonary arterial pressure in accordance with the present invention, attention is directed to FIG. 6 which depicts a functional flowchart of an exemplary manner of operating the pacemaker illustrated in FIGS. 4 and 5 in DDD pacing mode. For the sake of simplicity, functional steps corresponding to the provision of refractory and blanking periods have been omitted, to allow for easier understanding of the overall timing operational mode. In the flowchart of FIG. 6, it is assumed that the basic timing of the device is based around of the definition of an atrial escape interval (an A-A or V-A interval) which may be a fixed lower rate or may vary as a result of the output of an RCP(s) in a range between a lower rate limit and an upper rate limit.

At step 400, the atrial escape interval is reset and the current AV delay interval (SAV or PAV) is started, both in response to an atrial event (A-PACE or A-EVENT). At step 402, the AV delay interval time-out is monitored, and the system awaits either time out of the current AV delay interval (PAV or SAV) and the triggering of a V-PACE at step 404 or a V-EVENT at step 406. If a V-EVENT does not occur prior to AV delay interval time out, the V-PACE is generated at step 404, and the values of the AV delay intervals are updated, if necessary, at step 410. If a V-EVENT occurs at step 406 prior to expiration of the current AV delay interval, the timing may optionally be reset at step 408 to deliver an A-PACE at a V-A escape interval thereafter equal to the overall A-A escape interval minus the current AV delay interval. Alternatively, the system may proceed directly to updating the base AV delay intervals at step 410, and not alter the timing of the next scheduled A-PACE at the expiration of the A-A escape interval.

Following update of the base AV delay intervals at step 410, the system awaits expiration of the atrial escape interval at step 412, occurrence of a non-refractory V-EVENT at step 420, or occurrence of an A-EVENT at step 422, outside of the atrial refractory period. If the atrial escape interval expires at step 412 without an A-EVENT or V-EVENT, an A-PACE pulse is generated at step 414. The next succeeding AV delay interval is defined to be equal to PAV at step 416, followed by reset of the atrial escape interval and the AV delay interval at step 400.

If a V-EVENT is sensed at step 420, prior to expiration of the atrial escape interval, the atrial escape interval timing is reset at step 418. The V-EVENT sensed at this point is not effective to trigger an update of the SAV and PAV intervals. If an A-EVENT is sensed at step 422, prior to expiration of the atrial escape interval, the subsequent AV delay interval is defined to be equal to SAV at step 424, and the atrial escape and AV delay intervals are reset at step 400.

As described above, the SAV and PAV delay intervals may differ from one another and may either be fixed or vary from a programmed-in lower rate AV delay interval as a function of the sensed atrial rate or a signal derived from the RCP(s). In accordance with the present invention, when the intrinsic or paced atrial heart rate is stable over a period of time sufficient to allow the PAP to stabilize and remains stable for the duration of an AV optimization operation of FIGS. 7 and 8, an optimal SAV or PAV delay time interval can be derived from an average minimum EPAD. The optimization algorithm is entered and continued as long as a string of successive A-PACEs or A-EVENTs continue at steps 414 or 422 as described below. Assuming for the moment that the atrial heart rate remains stable for an initial period, this means that the algorithm is entered after steps 414 or 422 of FIG. 6. Until the optimization algorithm is completed, the SAV or PAV delay interval is supplied during the optimization algorithm.

At this juncture, it should be noted that if the patient's heart is in third degree block, the intrinsic or paced atrial depolarization is not conducted to the ventricles. Consequently, the AV delay interval always ends with a V-PACE being delivered at step 404 of FIG. 6. The present invention directed to the optimization of the SAV or PAV is of greatest benefit to such patients, because otherwise if the V-EVENT is sensed during a test AV delay interval, it may not be possible to vary the test AV delay interval over a usefully wide range to find the optimum AV delay time interval. On the other hand, if ventricular conduction is present and terminates a certain, relatively long, test AV delay interval, there may be still be benefit in the determination of a shorter AV delay interval that shows improved hemodynamic pulmonary blood pressure over that prevalent at the end of the intrinsic AV delay interval.

Under these conditions, the optimization algorithm of FIGS. 7 and 8 may be entered into automatically and periodically for a time period starting at a programmed-in time of day, for example, as long as the paced or intrinsic atrial heart rhythm is stable. The microcomputer 302 (or a separate timer in the digital controller/timer circuit 330) maintains the time(s) of day and the total optimization time length (in minutes) that the optimization method is enabled. At the specified or programmed-in time of day, the intrinsic atrial rate may be monitored to determine if it is stable or the intrinsic atrial rate may be overdriven at a shortened atrial escape interval to ensure a stable rate.

In the alternative case, the optimization program may be initiated whenever the atrial intrinsic or paced rate is determined to be stable. In this regard, the digital timer/controller circuit 330 includes a stability counter 366 that is responsive to atrial interval timer 368. The atrial interval timer 368 is started on a V-EVENT or V-TRIG and terminated on an A-TRIG or the next V-SENSE or A-SENSE. Successive atrial intervals are compared to one another and a small delta value defining stability criteria. The count of stability counter 366 is incremented by those atrial intervals satisfying the stability criteria and as long as V-EVENTs do not occur.

Alternatively or additionally, the optimization algorithm may be invoked by a physician when the patient's intrinsic atrial rate is stable or using a programmer to temporarily overdrive the atrial intrinsic rate, if present, to obtain a stable paced atrial heart rate. The initial determination of an optimum AV delay interval for one or more stable atrial heart rates may be conducted by the physician upon implantation of the DDD pacemaker in a patient in the process of programming an initial optimum AV delay interval. Optimum SAV and the PAV delay intervals may both be established at that time and stored for use by the AV interval timer 372 until the next time that the AV delay interval is optimized. From time to time, the physician may again use the programmer to read out the current AV delay intervals and to invoke the operation of the optimization algorithm to check for any changes.

Any of these scenarios may occur or be initiated in the same pacemaker in the same patient at different atrial rates. In each case, when an indication of a stable atrial heart rate is obtained, and as long as it is maintained in completing the steps of the optimization algorithm, the pressure signal processor 380 is enabled by an activate pressure signal processor command. The resulting SAV and PAV values and EPAD measurements are stored in RAM in RAM/ROM unit 314 for use by the AV interval timer 372 in the algorithm of FIG. 6 on a FIFO basis. A historic record may be maintained of prior SAV and PAV values, the corresponding EPAD values, the heart rate, the time and date of storage, and other pacemaker operating conditions, for interrogation by the physician during a subsequent patient follow-up visit.

In any of these scenarios, the optimization algorithm of FIGS. 7 and 8 is invoked at step 700 with a pre-existing AV delay interval, referred to as "AVopt", which may be a previously optimized SAV or PAV delay interval for the prevailing atrial intrinsic or paced rate. For this reason, the starting AV delay interval is also referred to as AVopt in step 700, but the "Optimized" flag is set from "Yes" to "No" when the algorithm is commenced to determine the current AVopt delay interval and corresponding current EPADmin value. As stated above, the pressure signal processor 330 is enabled to power the implanted absolute pressure sensor 160 and to demodulate the pressure signal and provide the RVP and dP/dt signals. At step 702, EPAD is measured, over X successive beats or atrial intervals while monitoring the stability of the heart rate in step 704 using stability counter 366. If atrial heart rate is slow to stabilize, the stability criteria satisfaction is awaited in step 706 before the EPAD measurement commences in step 704. When stability criteria are satisfied, "X" EPAD values are averaged in step 708 and saved in RAM as the starting EPADmin at the starting AVopt delay interval.

Then, the starting AVopt delay interval is decremented by a value "Y" in step 710, and the decremented, test AV delay interval is compared to a minimum (AVmin) delay interval in step 712. If the comparison shows that the AV delay= AVmin in step 712, then the measurement of EPAD values at a set of test AV delay intervals shorter than the starting AVopt value is completed. The algorithm restarts at step 714 under the conditions of step 700 and then commences incrementing test AV delay intervals in step 800 of FIG. 8 described below. Assuming that the test AV delay interval is greater than AVmin, EPAD values are measured over X atrial heart beats at the test AV delay interval while monitoring atrial heart rate stability in step 716. Again, if stability criteria are not fully satisfied at each test AV delay interval at step 718, the return to stability is awaited in step 720. If atrial heart rate at the decremented test AV delay is stable over X heart beats, the EPAD values are again averaged in step 722 to derive an EPADtest value corresponding to the test AV delay interval in step 722. If the EPADtest value is less than an EPADmin value as determined at step 724 (indicating a hemodynamic improvement in AV synchrony), the Optimized flag is set to "Yes", the EPADtest value is stored as EPADmin, and the test AV delay interval is stored as AVopt in step 726. Steps 710–724 are then repeated for a new decremented test AV delay interval using the EPADmin value determined.

If EPADtest>EPADmin in step 724, then AV is set to AVopt in step 728. If the Optimized flag is set to "Yes" in step 730, the Optimized flag is reset to "No", and measurements are suspended for Z seconds in step 732. Steps 710–722 are then repeated for a new decremented test AV delay interval. Steps 730 and 732 indicate that the optimum AV delay interval has been determined, allowing the algorithm to time out over the Z seconds.

Turning to FIG. 8, steps 800–826 operate to provide EPADtest data corresponding to test AV delay intervals of increasing duration from the initial AVopt delay of step 700. The AV delay interval may be increased to a point where a conducted ventricular depolarization or an ectopic ventricular depolarization occurs before the test AV delay interval times out. At that point, it is not possible to determine an EPADtest value related to longer test AV delay intervals. At step 800, the test AV delay interval is incremented initially by adding an increment "Y" to AVopt. If a V-PACE does not occur in step 802, then a V-EVENT occurred, and the test AV delay is reset to AVopt, the Optimized flag is set to "No" and measurement is suspended for Z seconds in step 804. The algorithm loops back to step 710 to restart decrementing the test AV delay. The same operations of step 804 are undertaken if the test AV delay interval is found to be greater than a maximum AV delay interval AVmax in step 806.

Assuming neither condition prevails, the EPAD average values for the incremented test AV delay intervals are accumulated in steps 808–824 as in steps 716–732 described above. When the Optimized flag is set to "No" in step 824, the measurements are suspended Z seconds in steps 824 and 826, and the algorithm loops back to step 710 to again commence decrementing the test AV delay interval. Otherwise, the test AV delay interval is continually incremented until a V-EVENT occurs in step 802 or the AV delay interval exceeds the maximum interval in step 806.

The algorithm of FIGS. 7 and 8 is preferably automatically invoked whenever the patient's atrial heart rate is stable for the required time to complete the determination of the current AVopt delay interval in order to make the determination over a relatively narrow range of test AV delay intervals. Thus, during the patient's daily activities, the optimum AV delay may be determined on an ongoing basis. The pacemaker pulse generator may also be programmed to undertake a wider range determination of the optimum AV delay at a given time of day, e.g. when the patient is expected to be sleeping, in order to make certain that the AV delay interval has not been determined as a function of a local minimum EPAD value. As described below, the program may also be invoked by the physician during patient follow up visits to make a determination of the optimum AV delay interval using a wider range of test AV delay intervals to also ensure that a local minimum EPAD value has not influenced the automatic determination of the optimum AV delay.

Figure 9:
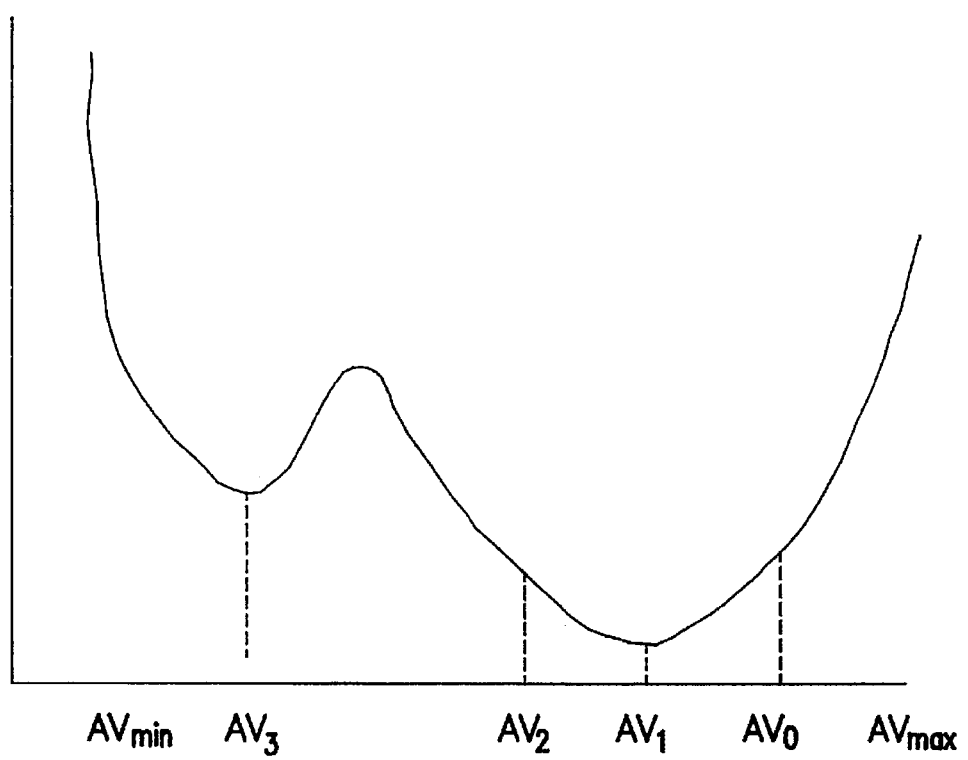
FIG. 9 is a graphical depiction of a hypothetical profile of EPAD values plotted against test AV delay intervals.

FIG. 9 depicts a hypothetical curve of EPAD test result values at a wide range of AV delay intervals. The curve of EPAD values is lowest at a true EPADmin value at $AV_1$ delay interval, and increases in the EPAD value occur at $AV_0$ and $AV_2$ delay intervals on either side of the $AV_1$ delay interval. Moreover, FIG. 9 shows a local minimum EPAD value at the $AV_3$ delay interval. The normal range of AV delay test values may be in the range between $AV_0$–$AV_2$. However, if it were centered around $AV_3$, the optimized AV delay interval would be centered on a local minimum EPAD value rather than the true minimum EPAD value. In accordance with one aspect of the invention, the wide range of AV delay intervals is tested periodically to ensure that such local minimum EPAD values are not mistaken for the true minimum EPAD value.

Figure 10:
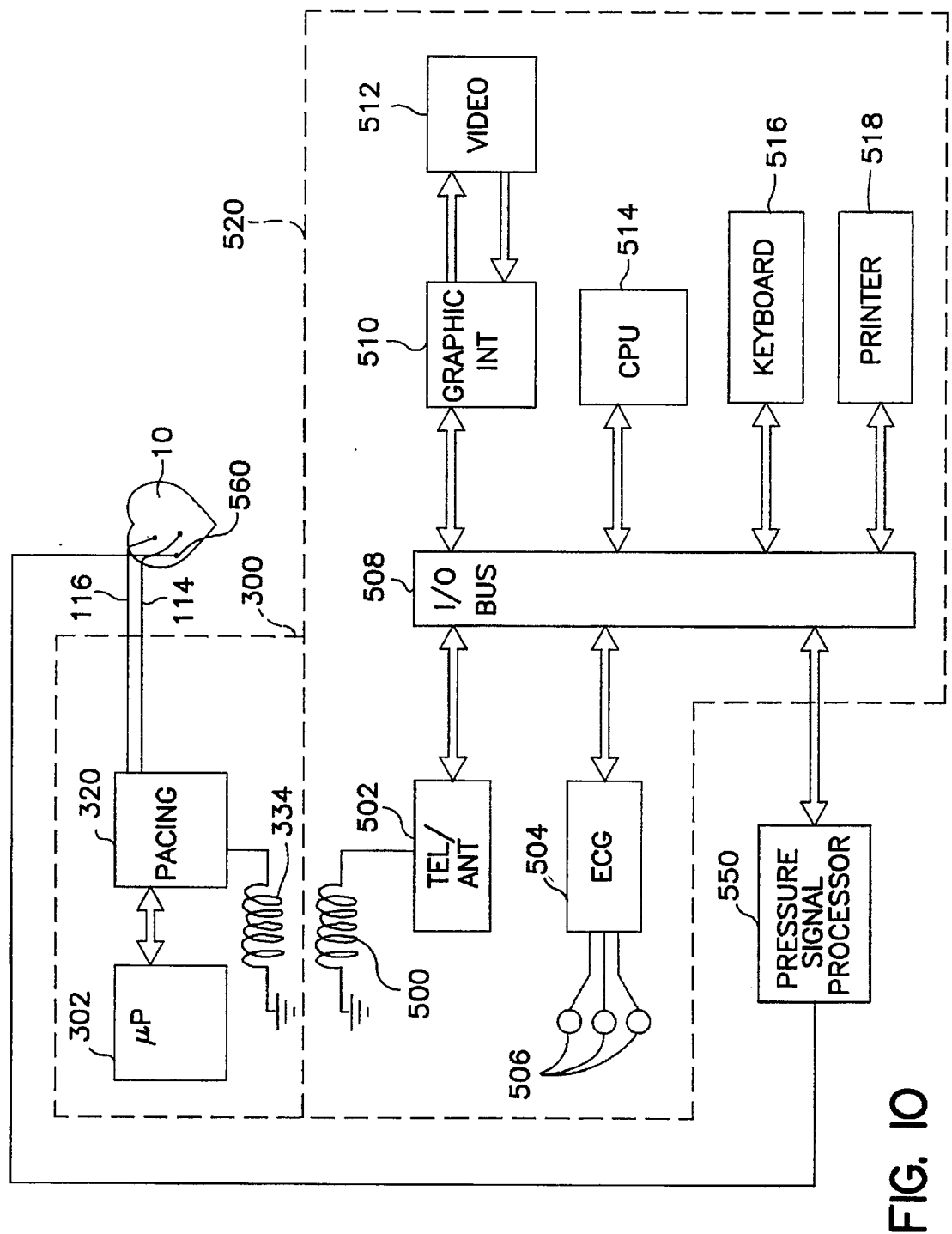
FIG. 10 is a block diagram of an external programmer for carrying out the process of optimizing the AV delay in accordance with the steps and means of FIGS. 7 and 8 in accordance with alternate embodiments of the invention.

Turning to FIG. 10, it depicts the components of a programmer 520 for effecting the initial manual programming of the algorithm of FIGS. 7 and 8 with a variation in block 550 that allows the algorithm to also be used in a typical DDD or DDDR pacemaker. First the use of the programmer 520 without block 550 will be explained with respect to the pacemaker of FIGS. 4 and 5 using an algorithm corresponding to the algorithm of FIG. 7 and 8 as described above to provide the initial determination of the optimum AV delay interval on implantation of the IPG 100 and the periodic determinations at patient follow-up visits with a wide range of test AV delay intervals to locate any local minimum EPAD phenomena.

FIG. 10 illustrates the IPG circuit 300 of FIG. 5 in more simplified block diagram form, coupled to human heart 10 through the leads 114, 116, in conjunction with the external programmer 520 corresponding to those typically employed to program modem, multi-programmable implantable pacemakers. The programmer 520 includes a telemetry antenna 500 coupled to a telemetry/antenna driver circuit 502 which serves to demodulate telemetry signals received from antenna 334 of the IPG 100, and to apply them in parallel or serial digital format to input/output (I/O) unit 508. The telemetry signals in turn may be applied to a video monitor 512, via graphics interface 510, and/or provided to central processing unit 514 and/or printer 518. Microprocessor 514 controls the operation of the programmer 520 and is responsive to physician entered commands via keyboard 516, for controlling programming signals sent via external telemetry antenna 500 to the telemetry antenna 334 of IPG 100 and operation of the video display 512 and printer 518. Also illustrated in FIG. 10 is an ECG interface 504 coupled to three ECG electrodes 506 which are intended to be placed upon the patient's body. ECG interface 504 provides sensed electrograms to input/output device 508, where they in turn may be provided to the video display 512, the central processing unit 514 or the printer 518.

In use, the physician initiates the commands for invoking the programmer-implemented AV delay test algorithm of FIGS. 7 and 8 in a temporary programming mode that can be terminated with a single command to restore permanently programmed values. The steps of the algorithm of FIGS. 7 and 8 can be carried out by successively programming in the decremented and incremented AV values through downlink telemetry and reading out the dP/dt and RVP values through uplink telemetry. The steps of deriving the average EPAD values can be effected in the programmer microcomputer 114 to create a printed record and/or a display on the video monitor 512 in the form of the curve of FIG. 9. When the optimum AV delay interval is determined, the physician can then program the optimum AV delay interval as a permanent starting AV delay for use by the IPG microcomputer 302 in association with the paced or intrinsic atrial rate. The same process can be repeated at other stable atrial rates to derive a family of starting AV delay intervals and, by extrapolation, to select an AV delay delta value for PAV and SAV delay intervals calculated at different sensor driven or intrinsic atrial rates.

As stated above, this process can be used with a wide range of test AV delays to ensure that local minimum EPAD values are not confused for the true minimum EPAD value as shown in FIG. 9. The test values may be displayed to the physician on the display 512 in the format of FIG. 9. Once the physician has determined or confirmed the optimum AV delay interval, the programmer 520 may also be employed to track and display the operation of the algorithm of FIGS. 7 and 8. In this regard, uplink telemetry may be invoked to telemeter out the EPAD values at each test AV delay interval in real time to provide an image of the program identifying the true minimum EPAD value on the display 512. For example, the EPAD values and test AV delay intervals corresponding to the portion of the curve of EPAD values between $AV_0$ and $AV_2$ of FIG. 9 may be shown on the display as they are developed to assure the physician that the algorithm is operating correctly with respect to the true EPADmin value.

Finally, the physician may program the internal AV delay optimization algorithm described above either on or off, and if on in either a periodic mode or in a continuous mode, dependent on determining a stable heart rate before searching for the optimum AV delay interval. As described at the outset, the algorithm may be used to modify any current AV delay that may itself vary with the patient's intrinsic atrial heart rate or sensor derived atrial heart rate.

Turning to a still further variation of the invention, the programmer 500 may also include an external blood pressure sensor for deriving the dP/dt and RVP values through use of a temporarily installed absolute pressure sensor 560 of one of the types described in the above-referenced Ohlson and Reynolds articles or in the cross-referenced U.S. patent application Ser. Nos. 08/394,870 filed Feb. 2, 1996, for IMPLANTABLE CAPACITIVE ABSOLUTE PRESSURE AND TEMPERATURE SENSOR and Ser. No. 08/394,860 filed Feb. 2, 1996, for IMPLANTABLE CAPACITIVE ABSOLUTE PRESSURE AND TEMPERATURE MONITORING SYSTEM. In this manner, the algorithm of FIGS. 7 and 8 may be practiced with a conventional DDD or DDDR pacemaker of the type described above. All of the operations of the algorithm may be effected employing the read-out pressure values and the temporary pacing modes available in such pacemakers.

The illustrated IPG block diagrams of the DDDR IPG circuit 300 of FIG. 5 and programmer 520 of FIG. 10 are merely exemplary, and correspond to the general functional organization of most multi-programmable, microprocessor controlled, DDD or DDDR cardiac pacemakers and programmers presently commercially available. It is believed that the present invention is most readily practiced in the context of such AV synchronous pacing systems, and that the present invention can therefore readily be practiced using the basic hardware of such existing microprocessor controlled, dual chamber pacemakers and programmers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacemaker having an architecture as illustrated in FIG. 5, and a circuit architecture as illustrated in FIG. 5 is not believed to be a prerequisite to enjoying the benefits of the present invention.

We claim:

1. In a dual chamber pacemaker pulse generator operating in accordance with an atrial-ventricular (AV) synchronous pacing method comprising the steps of:

timing a ventricular-atrial (V-A) pacing escape interval from a paced ventricular event;

delivering an atrial pace pulse to an atrium of a patient's heart at the time out of the V-A pacing escape interval unless an atrial sensed event occurs within said pacing escape interval;

prematurely terminating the V-A pacing escape interval on the sensing of an atrial sensed event within said V-A pacing escape interval;

timing an AV delay interval starting from a sensed atrial event or delivery of an atrial pace pulse;

delivering a ventricular pace pulse to a ventricle of the patient's heart at the termination of the AV delay interval unless a ventricular sensed event occurs within the AV delay interval;

prematurely terminating the AV delay interval on the sensing of a ventricular sensed event within the AV delay interval; and restarting the V-A pacing escape interval on a ventricular pace pulse or a ventricular sensed event, an AV delay interval optimization method for establishing an optimum AV delay interval for optimal left heart AV mechanical synchrony and function operable in conjunction with the AV synchronous pacing method steps comprising the further optimization method steps of:

(a) determining a stable atrial heart rate;

(b) on determination of a stable heart rate in step (a), continuing with steps (c)–(i) with an initial test AV delay interval;

(c) in the time period following a ventricular pace pulse delivered at the end of the initial test AV delay interval, measuring right ventricular blood pressure and providing a right ventricular pressure (RVP) signal;

(d) deriving a pressure rate of change signal (dP/dt) from the measured RVP signal;

(e) determining a peak amplitude of the dP/dt signal;

(f) measuring the RVP signal amplitude at the determined peak dP/dt signal as an estimated Pulmonary Artery Diastolic (EPAD) pressure;

(g) repeating steps (c)–(f) while a stable atrial heart rate continues with a set of adjusted test AV delay intervals changed by a predetermined delta value between a minimum and a maximum AV delay interval to derive a set of EPAD pressure values;

(h) identifying the test AV delay interval providing the lowest amplitude EPAD pressure value; and (i) selecting the identified test AV delay interval as the AV delay interval employed in the A-V synchronous pacing method.

2. The optimization method of claim 1 wherein said pacemaker pulse generator comprises means for programming operating modes thereof in response to programmed-in commands from an external programmer, and said optimization method further comprises the step of:

initiating said optimization method with a programmed-in command from said external pacemaker programmer.

3. The optimization method of claim 1 wherein said pacemaker pulse generator comprises timing means for providing a time of day, and said optimization method further comprises the step of:

initiating said optimization method at a predetermined time of day.

4. The optimization method of claim 1 wherein said pacemaker pulse generator comprises memory for storing AV delay intervals, and said optimization method further comprises the steps of:

measuring the stable atrial heart rate determined in step (a); and storing the test AV delay identified in step (h) in relation to the measured stable heart rate in memory;

and wherein the AV synchronous pacing method further comprises the step of retrieving from memory and employing the stored AV delay intervals corresponding to the V-A escape interval in timing the AV delay interval.

5. The optimization method of claim 4 wherein the AV synchronous pacing method further comprises:

determining a physiologic need for cardiac output from a rate control parameter;

establishing said V-A escape interval and said AV delay interval as a function of the determined physiologic need for cardiac output.

6. The optimization method of claim 1 wherein the AV synchronous pacing method further comprises:

determining a physiologic need for cardiac output from a rate control parameter;

establishing said V-A escape interval and said AV delay interval as a function of the determined physiologic need for cardiac output between a pacing lower rate and a pacing upper rate limit.

7. The optimization method of claim 1 further comprising the step of terminating the optimization method on the premature termination of the test AV delay interval by a ventricular sensed event.

8. In a dual chamber pacemaker, operating in accordance with the AV synchronous method comprising the steps of:

timing an escape interval from a paced or sensed ventricular event;

delivering an atrial pace pulse to an atrial chamber of a patient's heart at the termination of the escape interval unless an atrial sensed event occurs within said escape interval;

prematurely terminating said escape interval on the sensing of an atrial sensed event within said escape interval timing an atrial-ventricular (AV) delay interval from said sensed atrial event;

delivering a ventricular pace pulse to a ventricular chamber of the patient's heart at the termination of the AV delay interval unless a ventricular sensed event occurs within said AV delay interval; and restarting said escape interval on a ventricular pace pulse or a ventricular sensed event;

an AV delay interval optimization method for establishing an optimum AV delay interval for optimal left heart AV mechanical synchrony and function comprising the further steps of:

determining a stable atrial heart rate from a series of regular escape intervals;

in the AV delay test mode and in each of a succeeding series of regular escape intervals, selecting a test AV delay interval varying between a maximum AV delay interval and a minimum AV delay interval; and in the escape interval following the ventricular pace pulse delivered at the end of the test AV delay interval, determining the opening of the pulmonary valve and measuring right ventricular absolute blood pressure level at the moment of opening of the pulmonary valve;

identifying the AV delay interval providing the lowest measured ventricular absolute blood pressure level at the opening of the pulmonary heart valve; and selecting the identified AV delay interval as the AV delay interval associated with the intrinsic atrial depolarization rate of the heart.

9. The method of claim 8 wherein the step of determining the opening of the pulmonary valve following a ventricular sensed event or ventricular pace pulse further comprises:

processing the absolute pressure signal and providing a pressure rate of change signal; and determining a peak of the pressure rate of change signal signifying the slowing of the increase of the absolute pressure signal occurring on opening of the pulmonary valve.

10. The method of claim 8 wherein the step of determining a stable atrial heart rate from a series of regular escape intervals further comprises the steps of:

measuring the elapsed escape interval time to a premature termination by a sensed atrial event; and determining the occurrence a series of regular elapsed escape intervals terminating with an atrial sense event to commence an AV delay test mode.

11. In a dual chamber pacemaker operating in an atrial-ventricular (AV) synchronous pacing mode at a pacing rate dependent on a ventricular-atrial (V-A) pacing escape interval and an intrinsic V-A interval, an optimization method of establishing a set of optimized atrial-ventricular (AV) delay intervals for a corresponding set of V-A pacing escape intervals or intrinsic V-A intervals in a range between lower and upper pacing rate limits, each AV delay interval timed between a sensed or paced atrial event and a ventricular pace pulse delivered in the absence of a ventricular sensed event occurring during the AV delay interval, the optimization method comprising the steps of:

(a) from a preceding ventricular paced event, measuring the intrinsic V-A interval of a series of atrial sensed events;

(b) from the measured series of intrinsic V-A intervals, determining that the atrial heart rate is stable within a certain range and then continuing with steps (c) to (j);

(c) selecting a test AV delay interval;

(d) sensing right ventricular absolute pressure following a ventricular pace pulse at the end of the AV delay interval and providing an absolute pressure signal;

(e) determining the opening of the pulmonary valve from a characteristic change in the absolute pressure signal;

(f) measuring the absolute pressure signal level at the determined opening of the pulmonary valve;

(g) repeating steps (c)–(f) with a series of adjusted test AV delay intervals between a maximum AV delay interval and a minimum AV delay interval;

(h) comparing the absolute pressure signal levels measured in step (f);

(i) identifying the test AV delay interval providing the lowest measured absolute blood pressure level; and (j) selecting the identified AV delay interval as the AV delay interval associated with the atrial escape interval.

12. The optimization method of claim 11 wherein the step of determining the opening of the pulmonary valve further comprises:

processing the absolute pressure signal and providing a pressure rate of change signal; and determining a peak of the pressure rate of change signal signifying the slowing of the increase of the absolute pressure signal occurring on opening of the pulmonary valve.

13. The optimization method of claim 11 wherein said pacemaker pulse generator comprises means for programming operating modes thereof in response to programmed-in commands from an external programmer, and said optimization method further comprises the step of:

initiating said optimization method with a programmed-in command from said external pacemaker programmer.

14. The optimization method of claim 11 wherein said pacemaker pulse generator comprises timing means for providing a time of day, and said optimization method further comprises the step of:

initiating said optimization method at a predetermined time of day.

15. The optimization method of claim 11 wherein the AV synchronous pacemaker pulse generator further comprises:

means for determining a physiologic need for cardiac output from a rate control parameter; and means for establishing said V-A escape interval and said AV delay interval as a function of the determined physiologic need for cardiac output.

16. The optimization method of claim 11 further comprising the step of terminating the optimization method on the premature termination of the test AV delay interval by a ventricular sensed event.

17. The optimization method of claim 11 wherein step (b) further comprises:

determining a stable atrial heart rate from a series of timed out V-A pacing escape intervals or a series of atrial sensed events terminating V-A pacing escape intervals at a stable intrinsic interval from the preceding ventricular pace or sensed event.

18. In a dual chamber pacemaker pulse generator operable in an atrial-ventricular (AV) synchronous mode of the type having:

means for sensing atrial depolarizations of the heart and providing atrial sensed events;

means for sensing ventricular depolarizations of the heart and providing ventricular sensed events;

means for generating ventricular pace pulses on the time-out of an AV delay interval;

means for terminating the AV delay on sensing a ventricular depolarization during the time out of the AV delay interval;

means for timing a ventricular-atrial (V-A) pacing escape interval from a ventricular sensed event or generation of a ventricular pace pulse that may be terminated by an atrial sensed event; and means for generating atrial pace pulses at the termination of the V-A pacing escape interval;

the improvement in apparatus for optimizing the AV delay interval for a given atrial heart rate as a function of pulmonary blood pressure level to ensure optimum timing of ventricular pacing pulses and optimum AV mechanical synchrony in the left heart further comprising:

means for determining the occurrence of a regular atrial heart rate;

means for adjusting the length of said AV delay interval;

means operable following delivery of a pacing pulse at the end of the adjusted AV delay interval for measuring right ventricular absolute blood pressure during said pacing escape interval;

means for determining the adjusted AV delay interval providing the lowest right ventricular absolute blood pressure at the moment of opening of the pulmonary valve; and means for selecting said determined AV delay interval for use with said given pacing escape interval in the AV synchronous mode of the pacemaker pulse generator.

19. In a dual chamber pacemaker operating in an atrial-ventricular (AV) synchronous pacing mode at a pacing rate dependent on a ventricular-atrial (V-A) pacing escape interval and an intrinsic V-A interval, an optimization system for establishing an optimized atrial-ventricular (AV) delay interval for a corresponding V-A pacing escape intervals or intrinsic V-A interval in a range between lower and upper pacing rate limits, each AV delay interval timed between a sensed or paced atrial event and a ventricular pace pulse delivered in the absence of a ventricular sensed event occurring during the AV delay interval, the system comprising:

means for determining that the atrial heart rate is stable within a certain range;

means for selecting a test AV delay interval from among a plurality of test AV delay intervals within a range between a maximum test AV delay interval and a minimum test AV delay interval;

means for sensing right ventricular absolute pressure within the right ventricle following a ventricular pace pulse at the end of the AV delay interval and providing an absolute pressure signal;

means for determining the moment of opening of the pulmonary valve from a characteristic change in the absolute pressure signal;

means for measuring the absolute pressure signal level at the determined moment of opening of the pulmonary valve;

means operable while the heart rate remains stable for measuring a plurality of absolute pressure values at the determined moments of opening of the pulmonary valve in relation to said plurality of test AV delay intervals within said range between said maximum and minimum test AV delay intervals;

means for identifying the test AV delay interval within said range providing the lowest measured absolute blood pressure level; and means for selecting the identified AV delay interval as the AV delay interval associated with the atrial escape interval.

20. The optimization system of claim 19 wherein the means for determining the moment of opening of the pulmonary valve further comprises:

means for processing the absolute pressure signal and providing a pressure rate of change signal; and means for determining a peak of the pressure rate of change signal signifying the slowing of the increase of the absolute pressure signal occurring on opening of the pulmonary valve.

21. The optimization system of claim 19 wherein said pacemaker pulse generator comprises means for programming operating modes thereof in response to programmed-in commands from an external programmer, and said optimization system further comprises:

means for initiating said optimization method with a programmed-in command from said external pacemaker programmer.

22. The optimization system of claim 19 wherein said pacemaker pulse generator comprises timing means for providing a time of day, and said optimization system further comprises:

means for initiating said optimization method at a predetermined time of day.

23. The optimization system of claim 19 wherein said pacemaker pulse generator further comprises:

means for determining a physiologic need for cardiac output from a rate control parameter; and means for establishing said V-A escape interval and said AV delay interval as a function of the determined physiologic need for cardiac output.

24. The optimization system of claim 19 further comprising means for terminating the optimization method on the premature termination of the test AV delay interval by a ventricular sensed event.

25. The optimization system of claim 19 wherein said stable heart rate determining means further comprises:

means for determining a stable atrial heart rate from a series of timed out V-A pacing escape intervals or a series of atrial sensed events terminating V-A pacing escape intervals at a stable intrinsic interval from the preceding ventricular pace or sensed event.

26. The optimization system of claim 19 wherein said stable heart rate determining means further comprises:

means for measuring the intrinsic V-A interval of a series of atrial sensed events following a series of ventricular pace pulses; and means for determining that the atrial heart rate is stable within a certain range from the measured series of intrinsic V-A intervals.

27. The optimization system of claim 19 wherein said pacemaker pulse generator comprises downlink telemetry means responsive to programmed-in commands from an external programmer, and said optimization system further comprises:

means for initiating said optimization method with a programmed-in command from said external pacemaker programmer; and means for selecting the maximum and minimum test AV delay intervals in response to programmed in commands from said external pacemaker programmer to provide a wide range of absolute pressure measurements to distinguish local minimum pressure values from true minimum pressure values among said plurality of absolute pressure values.

28. The optimization system of claim 27 wherein:

said system pacemaker pulse generator comprises means for providing uplink telemetry of said test AV delay intervals and said measured absolute blood pressure levels to said external programmer; and said external programmer further comprises means for displaying said telemetered absolute pressure values in relation to said range of test AV delay intervals.

* * * * *